(12) United States Patent
Pfeiffer et al.

(10) Patent No.: US 7,977,282 B2
(45) Date of Patent: Jul. 12, 2011

(54) CHEMICAL AMENDMENTS FOR THE STIMULATION OF BIOGENIC GAS GENERATION IN DEPOSITS OF CARBONACEOUS MATERIAL

(75) Inventors: Robert S. Pfeiffer, Parker, CO (US); Glenn A. Ulrich, Golden, CO (US); Roland P. DeBruyn, Highlands Ranch, CO (US); Gary Vanzin, Arvada, CO (US)

(73) Assignee: Luca Technologies, Inc., Golden, CO (US)

( * ) Notice: Subject to any disclaimer, the term of this patent is extended or adjusted under 35 U.S.C. 154(b) by 18 days.

(21) Appl. No.: 11/765,902

(22) Filed: Jun. 20, 2007

(65) Prior Publication Data

US 2007/0295505 A1    Dec. 27, 2007

Related U.S. Application Data

(63) Continuation-in-part of application No. 11/399,099, filed on Apr. 5, 2006, now Pat. No. 7,696,132.

(51) Int. Cl.
*C09K 8/60* (2006.01)
*E21B 43/22* (2006.01)

(52) U.S. Cl. ........... 507/201; 507/267; 166/246; 435/41

(58) Field of Classification Search .................. 507/201, 507/267; 166/246; 435/41
See application file for complete search history.

(56) References Cited

U.S. PATENT DOCUMENTS

| | | | |
|---|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 3,185,216 A | 5/1965 | Hitzman |
| 3,332,487 A | 7/1967 | Jones |
| 3,340,930 A | 9/1967 | Hitzman |
| 3,437,654 A | 4/1969 | Dix |
| 3,637,686 A | 1/1972 | Kokubo et al. |
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wilberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,666,605 A | 5/1987 | Minami et al. |
| 4,678,033 A | 7/1987 | Killough |
| 4,743,383 A | 5/1988 | Stewart et al. |
| 4,799,545 A | 1/1989 | Silver et al. |
| 4,826,769 A | 5/1989 | Menger |
| 4,845,034 A | 7/1989 | Menger et al. |
| 4,883,753 A | 11/1989 | Belaich et al. |
| 4,905,761 A | 3/1990 | Bryant |
| 4,906,575 A | 3/1990 | Silver et al. |
| 4,914,024 A | 4/1990 | Strandberg et al. |
| 4,947,932 A | 8/1990 | Silver et al. |
| 4,969,130 A | 11/1990 | Wason et al. |
| 4,971,151 A | 11/1990 | Sheehy |
| 5,044,435 A | 9/1991 | Sperl et al. |
| 5,076,927 A | 12/1991 | Hunter |
| 5,081,023 A | 1/1992 | Yaginuma et al. |

(Continued)

FOREIGN PATENT DOCUMENTS

DE    4036787 B1    5/1992

(Continued)

OTHER PUBLICATIONS

Ferry et al. 1976. Anaerobic Degradation of Benzoate to Methane by Microbial Consortium. Arch. Microbiol. 107, pp. 33-40.

(Continued)

*Primary Examiner* — Taeyoon Kim
(74) *Attorney, Agent, or Firm* — Kilpatrick Townsend & Stockton LLP

(57) ABSTRACT

Methods of stimulating biogenic production of a metabolic product with enhanced hydrogen content are described. The methods may include accessing a consortium of microorganisms in a geologic formation that includes a carbonaceous material. They may also include providing a phosphorous compound to the microorganisms. The phosphorous compound stimulates the consortium to metabolize the carbonaceous material into a metabolic product with enhanced hydrogen content. Also, methods of stimulating biogenic production of a metabolic product with enhanced hydrogen content by providing a yeast extract amendment to a consortium of microorganisms is described. The yeast extract amendment stimulates the consortium to metabolize carbonaceous material in the formation into the metabolic product with enhanced hydrogen content.

10 Claims, 23 Drawing Sheets

U.S. PATENT DOCUMENTS

| | | | |
|---|---|---|---|
| 5,083,610 A | 1/1992 | Sheehy |
| 5,083,611 A | 1/1992 | Clark et al. |
| 5,087,558 A | 2/1992 | Webster, Jr. |
| 5,100,553 A | 3/1992 | Nomura et al. |
| 5,155,042 A | 10/1992 | Lupton et al. |
| 5,163,510 A | 11/1992 | Sunde |
| 5,250,427 A | 10/1993 | Weaver et al. |
| 5,297,625 A | 3/1994 | Premuzic et al. |
| 5,327,967 A | 7/1994 | Jenneman et al. |
| 5,340,376 A | 8/1994 | Cunningham |
| 5,341,875 A | 8/1994 | Jenneman et al. |
| 5,350,684 A | 9/1994 | Nakatsugawa et al. |
| 5,360,064 A | 11/1994 | Jenneman et al. |
| 5,363,913 A | 11/1994 | Jenneman et al. |
| 5,368,099 A | 11/1994 | Davey et al. |
| 5,424,195 A | 6/1995 | Volkwein |
| 5,490,634 A | 2/1996 | Jain et al. |
| 5,492,828 A | 2/1996 | Premuzic et al. |
| 5,500,123 A | 3/1996 | Srivastava |
| 5,510,033 A | 4/1996 | Ensley et al. |
| 5,516,971 A | 5/1996 | Hurley |
| 5,538,530 A | 7/1996 | Heaton et al. |
| 5,551,515 A | 9/1996 | Fodge et al. |
| 5,560,737 A | 10/1996 | Schuring et al. |
| 5,593,886 A | 1/1997 | Gaddy |
| 5,593,888 A | 1/1997 | Glaze et al. |
| 5,597,730 A | 1/1997 | Aust et al. |
| 5,630,942 A | 5/1997 | Steiner |
| 5,670,345 A | 9/1997 | Srivastava et al. |
| 5,695,641 A | 12/1997 | Cosulich et al. |
| 5,723,597 A | 3/1998 | Kohne |
| 5,763,736 A | 6/1998 | Daume |
| 5,766,929 A | 6/1998 | Orolin et al. |
| 5,783,081 A | 7/1998 | Gaddy |
| 5,821,111 A | 10/1998 | Grady et al. |
| 5,854,032 A | 12/1998 | Srivastava et al. |
| 5,858,766 A | 1/1999 | Premuzic et al. |
| 5,885,825 A | 3/1999 | Lin et al. |
| 5,919,696 A | 7/1999 | Ikeda et al. |
| 5,928,864 A | 7/1999 | Kohne |
| 5,955,261 A | 9/1999 | Kohne |
| 5,955,262 A | 9/1999 | Kourilsky et al. |
| 6,090,593 A | 7/2000 | Fleming et al. |
| 6,143,534 A | 11/2000 | Menger et al. |
| 6,202,051 B1 | 3/2001 | Woolston |
| 6,210,955 B1 | 4/2001 | Hayes |
| 6,265,205 B1 | 7/2001 | Hitchens et al. |
| 6,348,639 B1 | 2/2002 | Crawford et al. |
| 6,420,594 B1 | 7/2002 | Farone et al. |
| 6,543,535 B2 | 4/2003 | Converse et al. |
| 6,758,270 B1 | 7/2004 | Sunde et al. |
| 6,795,922 B2 | 9/2004 | Johnson et al. |
| 6,859,880 B2 | 2/2005 | Johnson et al. |
| 7,696,132 B2 | 4/2010 | Pfeiffer et al. |
| 2001/0045279 A1 | 11/2001 | Converse et al. |
| 2003/0062270 A1 | 4/2003 | McAlister |
| 2003/0205458 A1 | 11/2003 | Roychowdhury |
| 2003/0216353 A1 | 11/2003 | Mosher et al. |
| 2003/0232423 A1 | 12/2003 | Priester et al. |
| 2004/0033557 A1 | 2/2004 | Scott et al. |
| 2004/0035785 A1 | 2/2004 | Rebholz |
| 2004/0228833 A1 | 11/2004 | Costantino et al. |
| 2005/0053955 A1 | 3/2005 | Sowlay et al. |
| 2005/0269261 A1 | 12/2005 | Sublette |
| 2006/0223153 A1 | 10/2006 | Pfeiffer |
| 2006/0223159 A1 | 10/2006 | Pfeiffer |
| 2006/0223160 A1 | 10/2006 | Vanzin |
| 2006/0237097 A1 | 10/2006 | Lau et al. |
| 2006/0254765 A1 | 11/2006 | Pfeiffer et al. |
| 2007/0248531 A1 | 10/2007 | Debryun et al. |
| 2008/0299635 A1 | 12/2008 | Pfeiffer et al. |
| 2010/0190203 A1 | 7/2010 | Pfeiffer et al. |
| 2010/0248321 A1 | 9/2010 | Steaffens et al. |
| 2010/0248322 A1 | 9/2010 | Pfeiffer et al. |

FOREIGN PATENT DOCUMENTS

| | | |
|---|---|---|
| DE | 4115435 B2 | 8/1992 |
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 B6 | 9/2001 |
| WO | WO 02/06503 A | 1/2002 |
| WO | WO 02/34931 A2 | 5/2002 |
| WO | WO 2004/071195 A1 | 8/2004 |
| WO | WO 2005/115648 A1 | 12/2005 |
| WO | WO 2007/022122 A1 | 2/2007 |
| WO | WO 2007/118094 A2 | 10/2007 |

OTHER PUBLICATIONS

International Search Report and Written Opinion, Oct. 1, 2008, pp. 1-12, PCT/US08/67227.

International Search Report and Written Opinion, Jul. 14, 2008, pp. 1-9, PCT/US07/065884.

Hunkeler et al., "Petroleum Hydrocarbon Mineralization in Anaerobic Laboratory Aquifer Columns," Journal of Contaminant Hydrology 32, pp. 41-61, 1998.

EP Supplemental Search Report mailed Nov. 5, 2010; Application No. 08771271.7, 6 pages.

Batelle and Duke Engineering and Services; *Surfactant-Enhanced Aquifer Remediation (SEAR) Design Manual*; NFESC Technical Report TR-2206-ENV, Apr. 2002, 110 pgs: entire document; Naval Facilities Engineering Command Washington, DC 20374-5065 USA.

Brauer, S. et al., "Methanogenesis in McLean Bog, an Acidic Peat Bog in Upstate New York: Stimulation by H2/CO2 in the Presence of Rifampicin, or by Low Concentrations of Acetate," (*Geomicrobiology Journal*, Oct.-Nov. 2004, vol. 21, No. 7, pp. 433-443(11)), http://www.ingentaconnect.com, printed Apr. 26, 2005, 2 pgs.

Braun, Harry, "The Bad News About Natural Gas," Hydrogen News, Mar. 15, 2003, 2 pgs.

CAN Europe, "Climate technology sheet #9: Hydrogen production," published Nov. 2003, pp. 1-10.

Dong, Wen-Sheng et al., "Hydrogen Production from Methane Reforming Reactions over Ni/MgO Catalyst," Bull. Korean Chem. Soc. 2001, vol. 22, No. 12, Aug. 11, 2001, 1 pg.

Dumitru, Razvan et al., "Targeting Methanopterin Biosynthesis to Inhibit Methanogenesis," Applied and Environmental Microbiology, vol. 69, No. 12, Dec. 2003, pp. 7236-7241.

Hydrogen production in oil field production fluids with inactive methanogens. Data to be considered for incorporation into Luca's hydrogen patent, unauthored text, Mar. 9, 2005, 2 pgs.

Karl Lang, "*Coalbed Methane Trends*," PTTC State-of-the-Art Technology Summary, Excerpts in PTTC Network News, 2nd Quarter 2000, http://www.pttc.org/tech_sum/statev6no2.htm, printed Mar. 26, 2004, pp. 1-6.

Lovley, Derek R. et al., "Use of Dissolved H2 Concentrations to Determine Distribution of Microbially Catalyzed Redox Reactions in Anoxic Groundwater," ES&T Research, Eviron. Sci. Technol., vol. 28, No. 7, 1994, pp. 1205-1210.

PCT International Search Report and Written Opinion mailed May 5, 2010; International Application No. PCT/US2010/028691; 12 pages.

Ulrich, Glenn A. et al., "Active Biogenesis", *Energy*, Spring 2005, XP008128250, pp. 21-26.

Zajic, J. E. et al., "Microbial Hydrogen Production From Replenishable Resources," Int. J. Hydrogen Engergy, vol. 4, published 1979, pp. 385-402.

Van Ginkel, S., et al., "Biohydrogen Production as a Function of PH and Substrate Concentration", Environmental Science and Technology, American Chemical Society, Easton, PA, USA, vol. 35, No. 24, Dec. 15, 2001, pp. 4726-4730.

EP Supplementary Search Report mailed October 12, 2010; Application No. 05747464.5; 7 pages.

Wantabe, K. et al., "Diversity and Abundance of Bacteria in An Underground Oil-Storage Cavity," BMC Microbiology, pp. 1-10, (2002).

Aitken, Carolyn M. et al. "Anaerobic hydrocarbon degradation in deep subsurface oil reserves" Nature, Sep. 16, 2004, pp. 291-294.

Anderson, Robert T., and Lovley, Derek R., "Hexadecane Decay my Methanogenesis," Nature, v. 404, p. 722,Apr. 13, 2000.

Anderson, Robert T., Rooney-Varga, Juliette N. et al., "Anaerobic Benzene Oxidation in the Fe(III) Reduction Zone of Petroleum-Contaminated Aquifers," Environmental Science & Technology, v. 32, pp. 1222-1229, 1998.

Artech Inc., Biological Gasification of Coals. Final Report, U.S. Department of Energy, Contact DE-AC21-87MC23285, pp. 40-63, 1990.

Basiliko, Nathan et al., "Influence of Ni, Co, Fe, and Na additions on methane production in Sphagnum dominated Northern American peatlands" Biogeochemistry, 2001, 52: 133-153.

Belyaev, S.S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Berenard, F.P. et al. "Indigenous Microorganisms in Connate Water of Many Oil Fields: A New Tool in Exploration and Production Techniques" SPE 24811, 1992, pp. 467-476.

Boone, David R. et al.—Bergey's Manual of Systematic Bacteriology—Second Edition—vol. One "The Archaea and the Deeply Branching and Phototrophic Bacteria," Springer, 4 pages, 2001.

Brockman, Fred "Regulation of Microbial Communities" at http://www.sysbio.org/sysbio/microbial/index.stm, 2005, 2 pages.

Brown, L.R., and Vadie, A.A., "Slowing production Decline and Extending the Economic Life of an Oil Field: New MEOR Technology," SPE 59306; SPE/DOE Improved Oil Recovery Symposium,Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Cervantes, Francisco J. et al., "Competition between methanogenesis and quinone respiration for ecologically important substrates in anaerobic consortia" FEMS Microbiology Ecology 34, 2000, pp. 161-171.

Claypool, George E. et al. "The Origin and Distribution of Methane in Marine Sediments" *Natural Gases in Marine Sediments,* Ed. Issac R.Kaplan, 1974, pp. 99-139.

Claypool, George E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.

Clayton et al. "Oil-Generating Coals of the San Juan Basin, New Mexico and Colorado, U.S." Org. Geochem. 1991, pp. 735-742, vol. 17, No. 6.

Clayton, C. et al. "Source Volumetrics of Biogenic Gas Generation" Bacterial Gas, Ed. R. Vially, 1992, pp. 191-204, Paris.

Coates, John D., Anderson, Robert T., et al., "Anaerobic Hydrocarbon Degradation in Petroleum-Contaminated Harbor Sediments under Sulfate-Reducing and Artificially Imposed Conditions," Environ. Sci. Techno., vol. 30, No. 9, pp. 2784-2789m 1996.

Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.

Connan, J. et al. "Origin of Gases in Reservoirs" 1995 International Gas Research Conference, 1996, pp. 21-41.

Conrad, R. "Contribution of hydrogen to methane production and control of hydrogen concentrations in methanogenic soils and sediments" FEMS Microbiology Ecology, 28 (1999) pp. 193-202.

DeBruin, R.H. et al. "Coalbed Methane in Wyoming" Wyoming State Geological Survey (Laramie, WY), Information Pamphlet 7 (second revision), 2004, 24 pages.

Donaldson et al., "Conference Focuses on Microbial Enhancement of Oil Recovery," The Oil and Gas Journal, pp. 47-52, Dec. 20, 1982.

Donaldson, Eric C. et al. Microbial Enhanced Oil Recovery, Developments in Petroleum Science, 1989, v. 22, pp. 1-14, 121, 123, 149,Elsevier.

Faber, E. et al. "Distinction of Bacterial and Thermogenic Hydrocarbon Gases" Bacterial Gas, Ed. R. Vially, 1992, pp. 63-74, Paris.

Flesner, R. et al. "Pilot-scale base hydrolysis processing of HMX-based plastic-bonded explosives", 4th International Symposium on Special Topics in Chemical Propulsion: Challenges in Propellants and 100 Years after Nobel, May 27-31, 1996, pp. 213-220.

Flesner, R. et al. "Pilot-scale base hydrolysis processing of HMX-based plastic-bonded explosives," Chemical Abstracts, vol. 130, No. 5, Feb. 1, 1998, Columbus, Ohio, U.S.: Abstract No. 54464a, pp. 835.

Gaasterland, Terry "Archaeal Genomics" Current Opinions in Microbiology (1999) 2:542-547.

Galagan, James E. et al. "The Genome of *M. acetivorans* Reveals Extensive Metabolic and Physiological Diversity," Genome Research 12: 532-542 (2002).

Grbic-Galic, D., and Vogel,T. "Transformation of Toluene and Benzene by mixed methanogenic cultures" Applied and Environmental Microbiology, 1987, v. 53, pp. 254-260.

Groudeva, V. I. et al. "Enhanced Oil Recovery by Stimulating the Activity of the Indigenous Microflora of Oil Reservoirs": Biohydrometallurgical Techynologies (Eds. Torma, A. E., Apel, M. L., and Brierlay, C. L.): Minerals, Metals, & Mater. Soc. Biohydromet. Technol. Int. Symp., 1993 (Jackson Hole, Wy. 93.8. 22-25) Proc. v. 2, pp. 349-356.

Gullapalli, Irene L. et al., "Laboratory Design and Field Implementation of Microbial Profile Modification Process", SPE Reservoir Evaluation & Engineering, v. 3, No. 1, pp. 42-49,Feb. 2000.

Halbouty, M. T. "East Texas Field—USA, East Texas Basin, Texas; in Stratigraphic Traps II" (compiled by N. H.Foster and E. A. Beaumont) AAPG Treatise of Petroleum Geology, Atlas of Oil and Gas Fields, 1991, pp. 189-206.

Hales, B. A. et al. "Isolation and Identification of Methanogen-specific DNA from Blanket Bog Peat by PCR Amplification and Sequence Analysis", Applied and Environmental Microbiology, 1996, pp. 668-675.

Hattori, Satoshi et al.; "Thermacetogenium phaeum gen.nov.,sp.nov., a strictly anaerobic, thermophilic, syntrophic acetate-oxidizing bacterium", International Journal of Systematic and Evolutionary Microbiology (2000), 50, 1601-1609, 9 pages, 2000.

Hermann, M. et al. "Anaerobic Microflora of Oil Reservoirs: Microbiological Characterization of Samples form Some Production Wells" BacterialGas (R. Vially Ed.) Editions Technip. Paris, 1992, pp. 223-233.

Hunkeler et al., "Petroleum Hydrocarbon Mineralization in Anaerobic Laboratory Aquifer Columns," Journal of Contaminant Hydrology 32, pp. 4161, 1998.

Ivanov, M. V. et al. "Additional Oil Production During Field Trials in Russia: Microbial Enhancement of Oil Recovery—Recent Advances" (4th US DOE MEOR Int Conf (Upton, NY, 1992) Proc; Elsevier Develop Petrol Sci Ser No. 39), 1993, pp. 373-381.

Ivanov, M.V. et al. "Die mikrobiologische Bildung von Methan in einer abzubauenden Erdollagerstatte" Frieberger Forschungshefte Reihe C., v., 1982, vol. 389, pp. 189-199.

Johnson, Ronald C. et al. A Preliminary Evaluation of Coalbed Methane Resources of the Wind River Indian Reservation, Wyoming: Coal-Bed Methane Potential of the Wind River Indian Reservation, Ed. Stephen Manydeeds, Dec. 1991, pp. 40-64, Bureau of Indian Affairs Division of Energy and Mineral Resources.

Johnson et al., 1991, "Preliminary Results of a Coalbed Methane Assessment of the Wind River Indian Reservation, Wyoming" Coalbed Methane, pp. 273-284.

Kasting, James F. "When Methane Made Climate" Scientific American, Jul. 2004, pp. 80-85.

Kim, Ann G. "Experimental Studies on the Origin and Accumulation of Coalbed Gas" U.S. Dept. of the Interior Bureau of Mines, Report of Investigations 8317, 1978, 18 pages.

Kim, Ann G. et al. "Hydrocarbon Gases Produced in a Simulated Swamp Environment" U.S. Dept. of the Interior Bureau of Mines, Report of Investigations 7690, 1972, 13 pages.

Klein, A. et al. "Comparative Analysis of Genes Encoding Methyl Coenzyme M Reductase in Methanogenic Bacteria", Mol Gen Genet, 1988, 213:409-420.

Krumholz, Lee R. et al. "Confined subsurface microbial communities in Cretaceous Rock" Nature (Mar. 6, 1997) pp. 64-66.

Kunzig, Robert "20,000 Microbes Under the Sea" Mar. 2004, pp. 32-41, vol. 25, No. 3.

Law, Ben E. et al. "Coalbed Gas Accumulations in the Paleocene Fort Union Formation, Powder River Basin, Wyoming" Coalbed Methane—1991; Rocky Mountain Association of Geologists, pp. 179-190.

Le Blanc, Leonard, Artificial Recharge, Offshore, p. 10, Feb. 2000.

L'Haridon, S., Reysenbach, A. L. et al., Hot Subterranean Biosphere in a Continental Oil Reservoir, Nature, v. 377, pp. 223-224, Sep. 21, 1995.

Li, M. et al. "Advances in Simulated Tests of Biogas" Oil & Gas Geology, 1996, v. vol. 17, No. 2, pp. 117-122, with abstract.

Lollar, B. Sherwood et al. "Evidence for bacterially generated hydrocarbon gas in Canadian Shield and Fennoscandian Shield rocks" Geochemical Cosmochimica Acta vol. 57, pp. 5073-5085 (1993).

Lomans, Bart P. et al. "Isolation and Characterization of *Mehanomethylovorans hollandica* gen. nov., sp. Nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.

Lovely, Derek R. "Deep Subsurface Microbial Processes" Reviews of Geophysics, 33.3 / Aug. 1995, pp. 365-381.

Magot, Michel et al. "Microbiology of Petroleum Reservoirs" Antonie van Leeuwenhoek, 2000, 77: 103-116.

Mattavelli, L. et al. "Deep Isotopic Light Methane in Northern Italy" Bacterial Gas, Ed. R. Vially, 1992, pp. 121-132.

McDonald, I. R. et al. "Molecular Ecological Analysis of Methanogens and Methanotrophs in Blanket Bog Peat" Microbial Ecology (1999) 38:225-233.

Nandi, R. et al. :Microbial Production of Hydrogen: An Overview Critical Reviews in Microbiology, 24 (1): 61-84 (1998).

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Neue, Heinz-Ulrich "Methane Emission from Rice Fields", BioScience, 1993, pp. 466-473, vol. 43, No. 7, downloaded from http://www.ciesin.org/docs/004-032/004-032.htnk.

Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.

O'Carroll, Christopher "The Pervasive Presence of Microbes" http://www.umassmag.com/Summer_2003/The-pervasive_presence_of_microbes_5_08.html 2003, 3 pages.

Orphan et al., "Culture-Dependant and Culture-Independent Characterization of Microbial Assemblages Associated with High-Temperature Petroleum Reservoirs," American Society for Microbiology, pp. 700-711, 2000.

Panow, A. et al. "Mechanisms of Biologically-Mediated Methane Evolution from Black Coal", Fuel Processing Technology v. 52, pp. 115-125, 1997.

Pedersen, K. "Exploration of Deep Intraterrestrial Microbial Life: Current Perspectives" FEMS Microbiology Letters 185 (2000) pp. 9-16.

Potter et al. "Artificial Recharge," Offshore, Feb. 2000, pp. 10.

Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 40732, 1990, pp. 193-202.

Reeve, John N. "Archaebacteria Then . . . Archaes Now (Are There Really No Archaeal Pathogens?)" Journal of Bacteriology, Vo. 181, No. 12, Jun. 1999, pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resources potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B. E., and Rice, D. D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981.

Rice, Dudley C. et al. "Identification and Significance of Coal-Bed Gas, San Juan Basin, Northwestern New Mexico and Southwestern Colorado" *Geology and Coal-Bed Methane Resources of the Northern San Juan Basin, Colorado and New Mexico*, Ed. J. Fassett, Coal-Bed Methane, San Juan Basin, 1988, pp. 51-59, Rocky Mountain Association of Geologists.

Rice, Dudley D. et al. "Nonassociated Gas Potential of San Juan Basin Considerable" Oil & Gas Jounral, Aug. 1990, pp. 60-61, vol. 88, No. 33.

Ridgley, J. L. et al. "Re-Evaluation of the Shallow Biogenic Gas Accumulation, Northern Great Plains, USA—Is The Similar Gas Accumulation In Southeastern Alberta And Southwestern Saskatchewan A Good Analog?" Summary Of Investigations (1999) vol. 1 pp. 64-78.

Rightmire, C. T. et al. "Coalbed Methane Resource", 1984, Coalbed methane resources of the United States, AAPG Studies in Geology #17, Tulsa, p. 1-B.

Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E. P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.

Rozanova, E. P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A. R., Intergas'95, "Limitations and Benefits of Microbially Enhanced Coalbed Methane"; May 15-19, 1995-The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

Scott, Andrew R, et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan Basin, Colorado and New Mexico", in S. D. Schwochow, D. K. Murrayi, and M. F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane". International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methans From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp, 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Volkwein, J. C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 19, 2004), pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: $CO_2$ reduction vs. acetate fermentation—Isotope evidence" Geochimica et Cosmochiica Acta, 1986, pp. 693-709, vol. 50, No. 5.

Zengler et al., "Methane Formation From Long-Chain Alkanes by Anaerobic Microorganisms," Nature, vol. 401, pp. 266-269, Sep. 16, 1999.

Zobell, C. E., "Bacterial Release of Oil From Sedimentary Materials," The Oil &Gas Journal, pp. 62-65, Aug. 2, 1947.

CHEMICAL AMENDMENTS FOR THE STIMULATION OF BIOGENIC GAS GENERATION IN DEPOSITS OF CARBONACEOUS MATERIAL

CROSS-REFERENCES TO RELATED APPLICATIONS

The present application is a continuation-in-part of U.S. patent application Ser. No. 11/399,099, filed Apr. 5, 2006, the entire contents of which are herein incorporated by reference for all purposes.

BACKGROUND OF THE INVENTION

Increasing world energy demand is creating unprecedented challenges for recovering energy resources, and mitigating the environmental impact of using those resources. Some have argued that the worldwide production rates for oil and domestic natural gas will peak within a decade or less. Once this peak is reached, primary recovery of oil and domestic natural gas will start to decline, as the most easily recoverable energy stocks start to dry up. Historically, old oil and gas fields are abandoned once the easily recoverable materials are extracted. These abandoned reservoirs, however, still contain significant amounts of energy containing carbonaceous material. The Powder River Basin in northeastern Wyoming, for example, is estimated to contain approximately 1,300 billion short tons of coal. Just 1% of the Basin's remaining coal converted to natural gas could supply the current annual natural gas needs of the United States (i.e., about 23 trillion cubic feet) for the next four years. Several more abandoned coal and oil resources of this magnitude are present in the United States.

As worldwide energy prices continue to rise, it may become economically viable to extract additional oil and coal from these formations with conventional drilling and mining techniques. However, a point will be reached where more energy has to be used to recover the resources than can be gained by the recovery. At that point, traditional recovery mechanisms will become uneconomical, regardless of the price of energy. Thus, new recovery techniques are needed that can extract resources from these formations with significantly lower expenditures of energy and costs.

One route for light hydrocarbon recovery that has received little commercial attention is biogenic conversion of carbonaceous materials in geologic formations into methane. As noted above, large potential sources of methane and other hydrocarbons with enhanced hydrogen content are locked up in the carbonaceous materials in coal, residual oil, etc. In biogenic conversion, microorganisms in the formation treat these carbonaceous materials as a food source and metabolize them into metabolic intermediates and products, such as alcohols, organic acids, aromatic compounds, hydrogen and methane, among others.

In many formations, however, the environmental chemistry does not favor the biogenic production of metabolic products like hydrogen and methane. In some of these formations, the presence of an inhibitor (e.g., saline) can prevent the microorganisms from metabolizing the carbonaceous substrate into the products. In other formations, the low concentration of one or more compounds (e.g., nutrient compounds) in the formation environment can slow or stop biogenic production of the products. In still other formations, a rise in concentration of a metabolic intermediate or product generated by an active consortium of microorganisms can slow additional metabolic activity.

Thus, there remains a need to identify chemical compounds that affect the rate of biogenic production of metabolic products by microorganisms in a formation environment. There also remains a need for methods of introducing chemical amendments to a geologic formation that will stimulate the biogenic production of the metabolic products in an efficient manner. These and other needs are addressed by the present invention.

BRIEF SUMMARY OF THE INVENTION

Embodiments of the invention include methods of stimulating biogenic production of a metabolic product with enhanced hydrogen content. The methods may include accessing a consortium of microorganisms in a geologic formation that includes a carbonaceous material. The methods may also include providing a phosphorous compound to the microorganisms. The phosphorous compound relieves a nutritional deficiency allowing the consortium to metabolize the carbonaceous material into a metabolic product with enhanced hydrogen content.

Embodiments of the invention also include additional methods of stimulating biogenic production of a metabolic product with enhanced hydrogen content. The methods may include accessing a consortium of microorganisms in a geologic formation that includes a carbonaceous material and providing a yeast extract amendment to the microorganisms. The yeast extract amendment stimulates the consortium to metabolize carbonaceous material in the formation into the metabolic product with enhanced hydrogen content.

Embodiments of the invention still also include methods of activating a consortium of microorganisms in a geologic formation to produce a metabolic product with enhanced hydrogen content. The methods may include accessing the consortium in the formation, providing a phosphorous and/or yeast extract compound amendment to the formation. The combination of the phosphorous compound amendment and the yeast extract amendment activates the consortium to metabolize carbonaceous material in the formation into the metabolic product with enhanced hydrogen content. Embodiments may also include transferring the activated consortium to regions of the same formation, or a different formation, which may contain less active consortia.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

Methods of stimulating the production of metabolic products with enhanced hydrogen content (e.g., gases such as hydrogen and methane) through chemical amendments are described. The amendments stimulate a consortium of microorganisms in a geologic formation to metabolize carbonaceous material in the formation into the metabolic products. The stimulation effects of the amendments may include increasing the rate of production of a metabolic intermediary and/or the metabolic product. They may also include activating a consortium in the formation to start producing the metabolic products. They may further include stopping or decreasing a "rollover" effect such as when the concentration of one or more metabolic products starts to plateau after a period of monotonically increasing. In addition, transfer and dilution of the activated consortium to other regions or formations may be done to generate an enriched consortium in a new region or formation with increased methanogenic activity. These and other stimulation effects may be promoted by the chemical amendments that are introduced by the methods of the invention.

Figure 1:
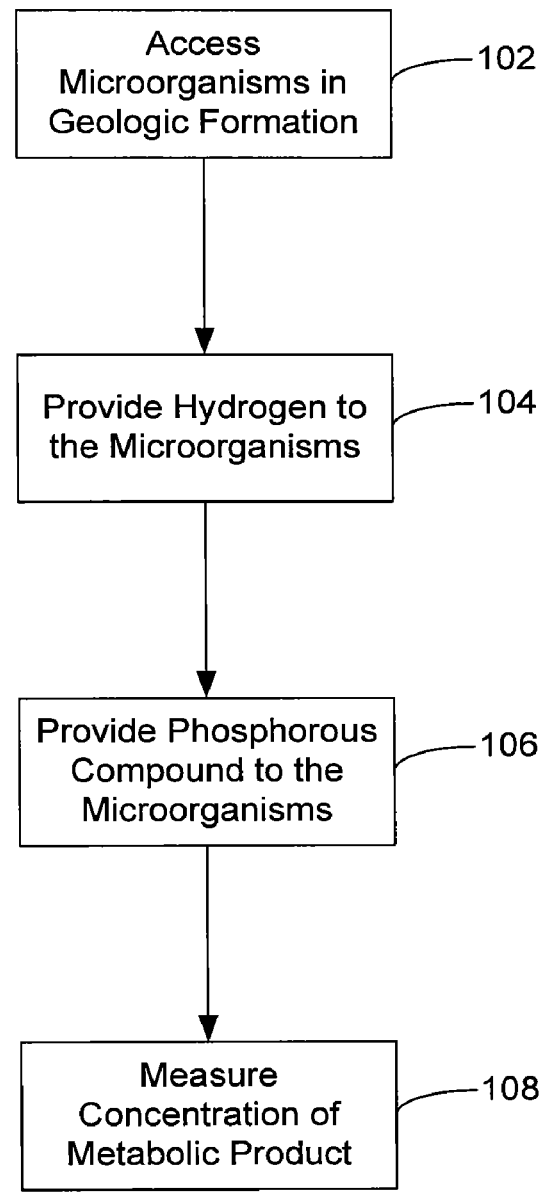
FIG. 1 is a flowchart illustrating a method of introducing hydrogen and phosphorous amendment to microorganisms in geologic formations according to embodiments of the invention.

Referring now to FIG. 1, a flowchart illustrating a method 100 of introducing hydrogen and phosphorous amendments to microorganisms in a geologic formation according to embodiments of the invention is shown. The method 100 includes accessing the formation water 102 in the geologic formation. The geologic formation may be a previously explored, carbonaceous material-containing subterranean formation, such as a coal mine, oil field, natural gas deposit, carbonaceous shale, etc. In many of these instances, access to the formation can involve utilizing previously mined or drilled access points to the formation. For unexplored formations, accessing the formation may involve digging or drilling thorough a surface layer to access the underlying site where the microorganisms are located.

Once access to the microorganisms in the formation is available, an amendment may be provided to them. In method 100, providing the amendment may include providing hydrogen to the microorganisms 104. Providing the hydrogen 104 may involve the direct injection of hydrogen gas into the formation region were the microorganisms are located. Alternatively (or in addition) a liquid, solid-phase, and/or aqueous hydrogen release compound may be provided to the formation. The compound can undergo a chemical or biochemical reaction in the formation that produces hydrogen gas in situ where the microorganisms reside. Examples of hydrogen release compounds may include polyacetate ester compounds that release lactic acid on contact with water. The lactic acid may then be metabolized by the microorganisms to produce organic acids (e.g., pyruvic acid, acetic acid, etc.) and hydrogen gas. Subsequent bioconversion of the organic acids may generate additional hydrogen. The hydrogen release compounds may also include solid-phase compounds containing zero valent iron particles. Hydrogen may also be generated by, for example, adding alcohols such as methanol and/or ethanol, and/or organic acids such as formic acid, acetic acid, propionic acid, butyric acid and/or lactic acid directly to the formation region in addition to (or in lieu of) other hydrogen generating amendments.

The amendment may also include providing one or more phosphorous compounds to the microorganisms 106. These phosphorous compounds may include phosphorous compounds (e.g., $PO_x$ compounds were x is 2, 3 or 4), such as sodium phosphate ($Na_3PO_4$) and potassium phosphate ($K_3PO_4$), as well as monobasic and dibasic derivatives of these salts (e.g., $KH_2PO_4$, $K_2HPO_4$, $NaH_2PO_4$, $Na_2HPO_4$, etc.). They may also include phosphorous oxyacids and/or salts of phosphorous oxyacids. For example, the phosphorous compounds may include $H_3PO_4$, $H_3PO_3$, and $H_3PO_2$ phosphorous oxyacids, as well as dibasic sodium phosphate and dibasic potassium phosphate salts. The phosphorous compounds may also include alkyl phosphate compounds (e.g., a trialkyl phosphate such as triethyl phosphate), and tripoly phosphates. The phosphorous compounds may further include condensed forms of phosphoric acid, including tri-polyphosphoric acid, pyrophosphoric acid, among others. They may also include the salts of condensed phosphoric acids, including alkali metal salts of tripolyphosphate (e.g., potassium or sodium tripolyphosphate), among other salts.

The hydrogen and phosphate may be provided to the formation in a single amendment, or they may be provided in separate stages. For example, if the phosphorous amendment takes the form of an aqueous solution, the solution may be injected into the formation with aid of compressed hydrogen gas. This allows the two components to be provided to the formation at substantially the same time. Alternatively, the hydrogen or phosphate amendment may be introduced first, followed by the introduction of the other compounds.

Whether the hydrogen and phosphorous compounds are introduced to the formation simultaneously or separately, they will be combined in situ and exposed to microorganisms. The combination of the hydrogen and phosphorous compound(s) can stimulate the microorganisms to metabolize carbonaceous material in the formation into metabolic products with enhanced hydrogen content, like methane. The enhanced hydrogen content products have a higher mol. % of hydrogen atoms than the starting carbonaceous material. For example, methane, which has four C—H bonds and no C—C bonds, has a higher mol. % hydrogen than a large aliphatic or aromatic hydrocarbon with a plurality of C—C single and double bonds. Additional details about compounds with enhanced hydrogen content may be found in co-assigned U.S. patent application Ser. No. 11/099,881, to Pfeiffer et al, filed Apr. 5, 2005, and entitled "GENERATION OF MATERIALS WITH ENHANCED HYDROGEN CONTENT FROM ANAEROBIC MICROBIAL CONSORTIA" the entire contents of which is herein incorporated by reference for all purposes.

Method 100 may further include adding additional amendments to the formation. For example, a yeast extract amendment may be added to provide nutrients to the microorganisms in the formation. The yeast extract may include digests and extracts of commercially available brewers and bakers yeasts.

Method 100 may also include measuring the concentration of a metabolic product 108. For gas phase metabolic products, the partial pressure of the product in the formation may be measured, while aqueous metabolic products may involve measurements of molar concentrations. FIG. 1 shows the measurement of metabolic products being made after the introduction of the hydrogen and phosphorous amendment. Measurements may also be made before providing the amendment, and a comparison of the product concentration before and after the amendment may also be made.

Figure 2:
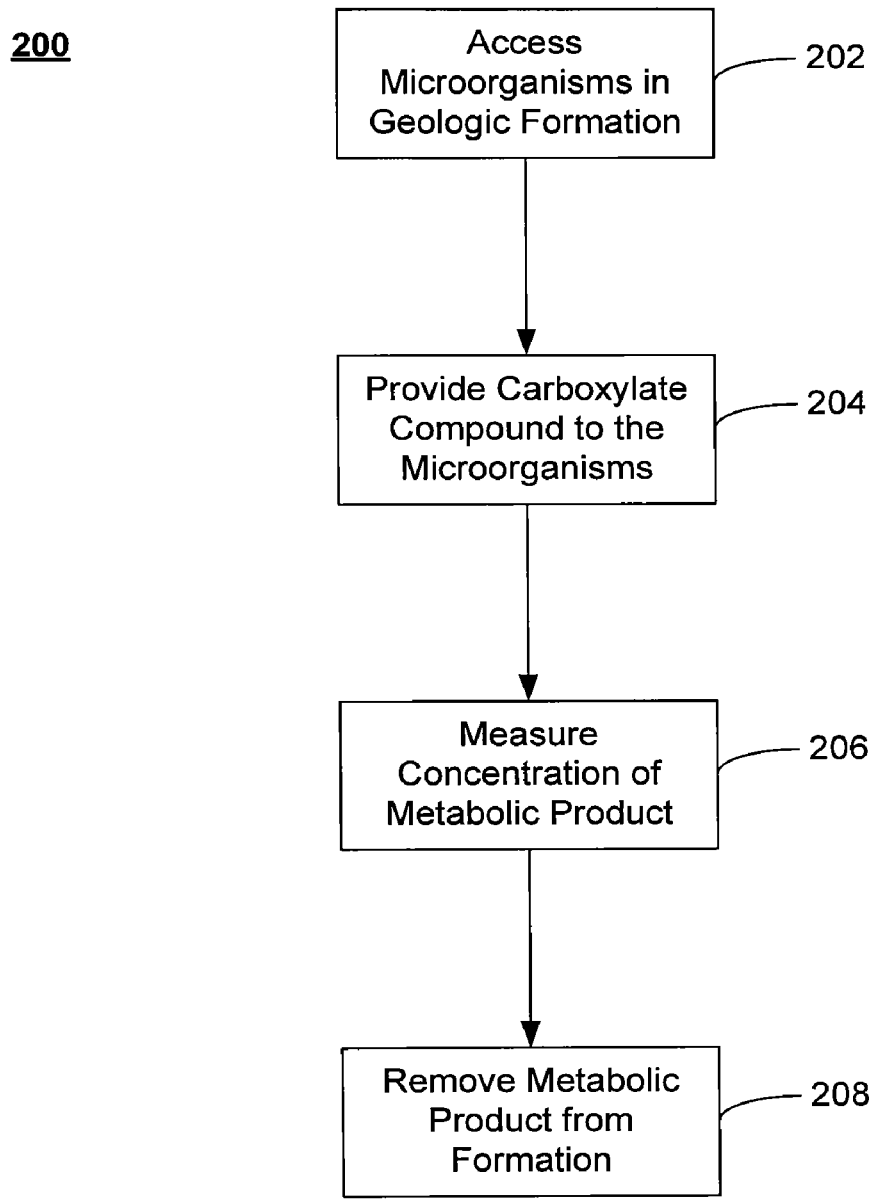
FIG. 2 is a flowchart illustrating a method of introducing carboxylate compound amendment to microorganisms in geologic formations according to embodiments of the invention.

FIG. 2 shows a method 200 of introducing a carboxylate compound amendment to microorganisms in geologic formations according to embodiments of the invention. The method 200 may include accessing the microorganism in the geologic formation 202. Once access is gained, one or more carboxylate compounds may be provided to the microorganisms in situ 204. The carboxylate compound may be an organic compound having one or more carboxylate groups (e.g., $COO^-$ groups). These compounds are typically organic acids or their salts. Examples include salts of acetate (i.e., $H_3CCOO^-$); benzoate (i.e., Ph-$COO^-$, where Ph is a phenyl group); and formate (i.e., $HCOO^-$), among other carboxylate groups. Additional amendments, such as a yeast extract amendment that provides nutrients to the microorganism in the formation, may also be provided.

The concentration of a metabolic product may be measured 206 following the introduction of the carboxylate compound. The product concentration may also be measured before the carboxylate compound is introduced, to determine the effect of adding the compound. In some instances, introducing the carboxylate compound to the microorganisms may cause an almost immediate increase in the production rate of the metabolic product. In other instances, there may be a period of delay between the introduction of the carboxylate compound and an increase in the production of the metabolic product. For example, the concentration of the metabolic product in the formation may stay at pre-introduction levels for about 30, 40, 50, 60, 70, or 80 days or more before significantly increasing. This may be easily monitored by following the concentration of an added non-degradable marker, for example bromide, over time.

A delay of several days or months between introducing the carboxylate compound and measuring a increase in the production of the metabolic product may be called the activation period. During this time, the presence of the carboxylate compound(s) may be influencing the population or metabolic pathways of the microorganisms. Very little (or even none) of the carboxylate compound may be metabolized by the microorganisms during the activation period. In these instances, the carboxylate compound may be acting as a catalyst that activates a metabolic pathway for the production of the metabolic product. Multiple introductions of the amendment may be made over the course of the activation period to maintain a concentration level of the amendment in the formation. Alternatively, the amendment can be pulsed into the formation using discontinuous injections. Experiments demonstrating activation of methane production with an acetate amendment are described in the Experimental section below.

Method 200 may also include removing the metabolic product 208 building up in the formation as a result of the carboxylate compound amendment. If the metabolic product is a gas such as hydrogen or methane, it may be removed with conventional natural gas recovery equipment. In some examples, the products may be removed through the same access points that were used to provide the carboxylate compound to the microorganisms. In additional examples, the products may be forced out of the formation by injecting a displacement fluid (e.g., nitrogen, water, etc.) into the formation.

Figure 3:
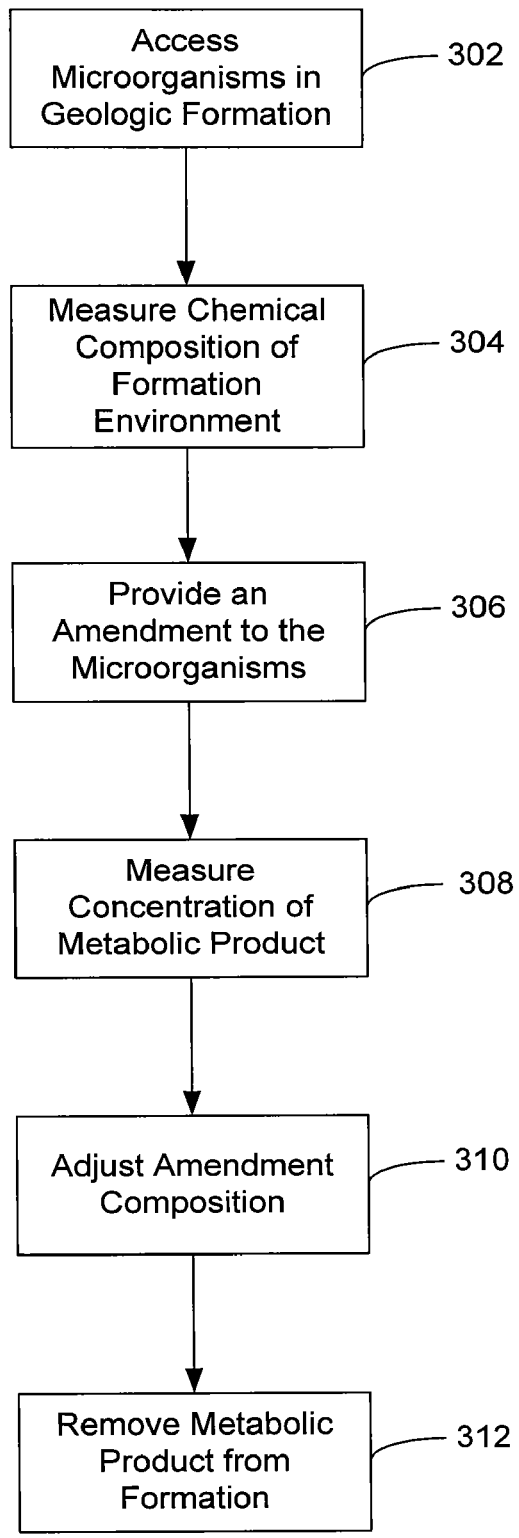
FIG. 3 is a flowchart illustrating a method of measuring the effects of introduced amendments on the production of metabolic products from geologic formations according to embodiments of the invention.

Referring now to FIG. 3, a flowchart illustrating a method 300 of measuring the effects of introduced amendments on the production of metabolic products from geologic formations is shown. The method 300 includes accessing the microorganisms 302 in a carbonaceous material containing geologic formation. Then an analysis of the microorganism formation environment may be conducted, which includes measuring the chemical composition that exists in the environment 304. This may include an in situ analysis of the chemical environment, and/or extracting gases, liquids, and solid substrates from the formation for a remote analysis.

For example, extracted formation samples may be analyzed using spectrophotometry, NMR, HPLC, gas chromatography, mass spectrometry, voltammetry, and other chemical instrumentation. The tests may be used to determine the presence and relative concentrations of elements like dissolved carbon, phosphorous, nitrogen, sulfur, magnesium, manganese, iron, calcium, zinc, tungsten, cobalt and molybdenum, among other elements. The analysis may also be used to measure quantities of polyatomic ions such as $PO_2^{3-}$, $PO_3^{3-}$, and $PO_4^{3-}$, $NH_4^+$, $NO_2^-$, $NO_3^-$, and $SO_4^{2-}$, among other ions. The quantities of vitamins, and other nutrients may also be determined. An analysis of the pH, salinity, oxidation potential (Eh), and other chemical characteristics of the formation environment may also be performed. Microorganism activity analyses may also be performed on extracted consortium samples. These analyses may include the use of $^{14}C$-acetate, $^{14}C$-bicarbonate, and other methanogen substrates to estimate methanogenic activity in samples including formation water collected before and during field applications. Additional details of analyses that may be performed are described in co-assigned PCT Application No. PCT/US2005/015259, filed May 3, 2005; and U.S. patent application Ser. No. 11/343,429, filed Jan. 30, 2006, of which the entire contents of both applications are herein incorporated by reference for all purposes.

A biological analysis of the microorganisms may also be conducted. This may include a quantitative analysis of the population size determined by direct cell counting techniques, including the use of microscopy, flow cytometry, plate counts, as wall as indirect techniques, such as DNA quantification, phospholipid fatty acid analysis, quantitative PCR, protein analysis, etc. The identification of the genera and/or species of one or more members of the microorganism consortium by genetic analysis may also be conducted. For example, an analysis of the DNA of the microorganisms may be done where the DNA is optionally cloned into a vector and suitable host cell to amplify the amount of DNA to facilitate detection. In some embodiments, the detecting is of all or part of ribosomal DNA (rDNA), of one or more microorganisms. Alternatively, all or part of another DNA sequence unique to a microorganism may be detected. Detection may be by use of any appropriate means known to the skilled person. Non-limiting examples include restriction fragment length polymorphism (RFLP) or terminal restriction fragment length polymorphism (TRFLP); polymerase chain reaction (PCR); DNA-DNA hybridization, such as with a probe, Southern analysis, or the use of an array, microchip, bead based array, or the like; denaturing gradient gel electrophoresis (DGGE); or DNA sequencing, including sequencing of cDNA prepared from RNA as non-limiting examples. Additional details of the biological analysis of the microorganisms is described in co-assigned U.S. patent application Ser. No. 11/099,879, filed Apr. 5, 2005, the entire contents of which is herein incorporated by reference for all purposes.

The method 300 also includes providing an amendment to the microorganisms in the formation 306. Embodiments of the present invention include providing amendments of hydrogen, phosphorous compounds, and/or carboxylate compounds (e.g., acetate) to the microorganisms. The amendments may also include vitamins, minerals, metals, yeast extracts, and other nutrients. The amendments may still further include water amendments to dilute metabolic inhibitors and/or the microorganism consortium.

The effect of the amendments can be analyzed by measuring the concentration of a metabolic intermediary or metabolic product 308 in the formation environment. If the product concentration and/or rate of product generation does not appear to be reaching a desired level, adjustments may be made to the composition of the amendment 310. For example, if an acetate amendment does not appear to be activating the microorganisms after a set period of time (e.g., 90 days or more), a different amendment may be introduced to stimulate the microorganisms (e.g., hydrogen and/or phosphorous compounds).

The method 300 may also include removing the metabolic product 312 from the formation. Removal may be triggered when the concentration of the reaction product increases above a threshold level in the formation. In some of these instances, removal may performed to keep the product in a concentration range that has been found to stimulate the microorganisms to generate more of the product.

Figure 4:
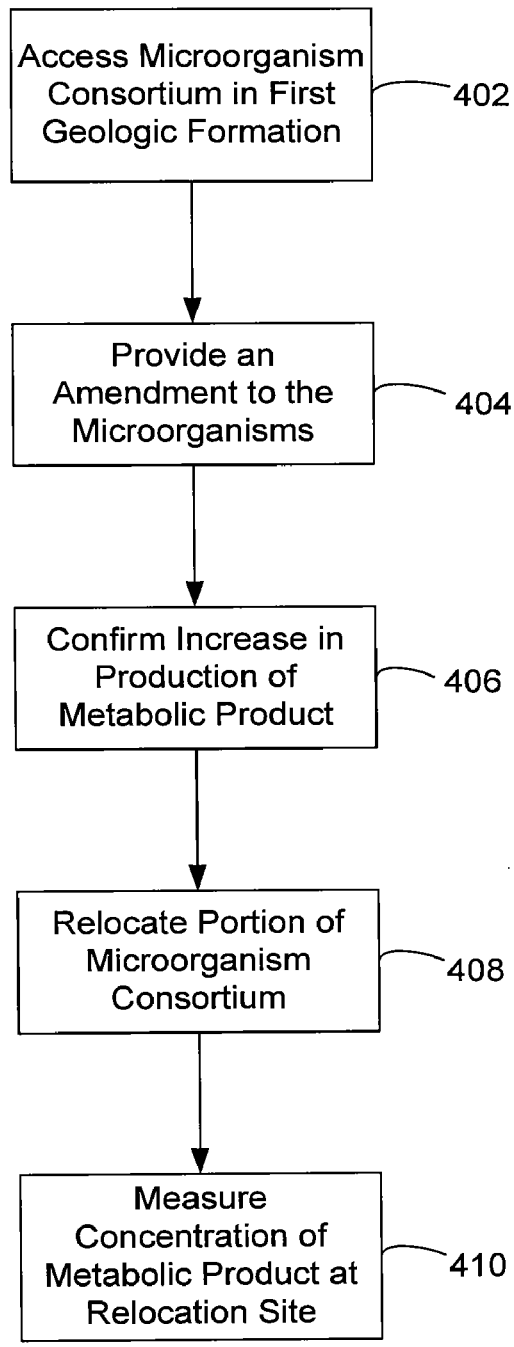
FIG. 4 is a flowchart illustrating a method of relocating a portion of an activated microorganism consortium from a first geologic formation according to embodiments of the invention.

FIG. 4 shows a flowchart illustrating an example of a method 400 of relocating a portion of an activated microorganism consortium from a first geologic formation according to embodiments of the invention. The method 400 includes accessing a microorganism consortium 402 in the geologic formation. As noted above, geologic formation may be a previously explored, carbonaceous material-containing subterranean formation, such as a coal mine, oil field, natural gas deposit, carbonaceous shale, etc. In many of these instances, access to the formation can involve utilizing previously mined or drilled access points to the formation. For unexplored formations, accessing the formation may involve digging or drilling thorough a surface layer to access the underlying site where the microorganisms are located. Access to the formation may also be gained through naturally-occurring features including formation outcrops that breach a land surface.

Method 400 also includes providing an amendment 404 to the microorganisms in the consortium. The amendment may include providing a phosphorous compound to the microorganisms, such as one or more of the phosphorous compounds described above. Compounds that are soluble in water may be added to an amount of water that is injected into the geologic formation and provided to at least a portion of the microorganisms in the consortium. In another example, the amendment provided to the consortium may include yeast extract. The yeast extract amendment may include brewer's yeast extract, a baker's yeast extract, a protein hydrolysate, blood meal, fish meal, meat and bone meal, beef peptone, or products of barley, beet, corn, cottonseed, potato, wheat, oat, soybean, and mixtures thereof. The yeast extract may be added as a solution or suspension to water that is injected into the geologic formation. In still another example, the phosphorous compound and yeast extract may both be added to the formation, simultaneously or separately, and exposed to at least a portion of the microorganism consortium. In still further examples the phosphorous compound and yeast extract, either alone or in combination, may be added with one or more additional amendments (e.g., hydrogen, acetic acid, minerals, metals, vitamins, etc.) to the geologic formation and provided to microorganisms.

Following the introduction of the amendment, one or more metabolic products related to methanogenesis may be monitored to confirm an increase in the production of the product 406. The assumption is that a production increase of the product within a short time (e.g., days, weeks, etc.) after the introduction of the amendment was caused by the amendment. The amendment stimulated the microorganisms to metabolize carbonaceous material in the formation into metabolic products with enhanced hydrogen content, like methane. As noted above, the enhanced hydrogen content products have a higher mol. % of hydrogen atoms than the starting carbonaceous material.

The confirmation of a significant increase in the production of a metabolic product, like methane following the introduction of an amendment indicates a microorganism consortium is active in at least a part of the geologic formation. Method 400 includes the step of relocating a portion of the active consortium 408 to a relocation site, which may be in another part of the same geologic formation, or in a different geologic formation. It has been observed that, under the right environmental conditions, the introduction of microorganisms from an active consortium to a location with reduced methanogenic activity can boost methanogenic activity at the new location. Additional details on systems and methods of transporting methanogenic microorganisms can be found in co-assigned U.S. patent application Ser. No. 11/343,429 to Pfeiffer et al, filed Jan. 30, 2006, and titled "BIOGENIC FUEL GAS GENERATION IN GEOLOGIC HYDROCARBON DEPOSITS" the entire contents of which are herein incorporated by reference for all purposes. The stimulation of methanogenic activity at the new location may be evidenced by measuring the concentration of a metabolic product at the relocation site 410.

In additional embodiments, removal of the metabolic product may be done independently of the product concentration in the formation. For example, the reaction products may be continuously removed from the formation as part of a process that cycles the amendment through the formation. The mixture of metabolic products, amendment components and other materials removed from the formation may be processed to separate the products from components that will be sent back into the formation.

EXPERIMENTAL

Hydrogen and Phosphorus Compound Amendments

Experiments were conducted to compare biogenic methane generation from coal samples after introducing an amendment of hydrogen gas, a phosphorous compound, and ammonia. For each experiment, methane generation from coal samples from the Monarch coal seam in the Powder River Basin in Wyoming was periodically measured over the course of about 627 days. Each anaerobic 5 gram coal sample was placed in a nominal 36.5 ml serum bottle with 15 mL of anaerobic water that was also taken from the formation. The coal and formation water were placed in the serum bottle while working in an anaerobic glove bag. The headspace in the bottle above the sample was flushed with a mixture of $N_2$ and $CO_2$ (95/5).

Amendments were then added to the samples. In a second set of experiments, 4.5 mL of $H_2$ gas (i.e., 179 µmol of $H_2$) was added to each bottle. Also added to the bottles was 0.15 mL of a 2500 mg/L (as N) aqueous ammonium chloride solution to provide a concentration of 25 mg/L, as nitrogen, to the samples, and 0.04 mL of a 1800 mg/L potassium phosphate solution that provided a concentration of 5 mg/L, as phosphate, to the samples. In a second set of experiments, the same amount of $H_2$ was added to the bottles, but no ammonium chloride or potassium phosphate. A third set of experiments introduced the ammonium chloride and potassium phosphate at the same levels as the first set, but no hydrogen gas was added. The samples were then sealed, removed from the glove bag, and stored at room temperature over the course of the experiments.

The methane levels in the headspace above the samples was periodically measured and recorded. The methane was measured by running samples of the headspace gases through a gas chromatograph equipped with a thermal conductivity detector. The highest levels of methane production after 627 days occurred in samples treated with an amendment of hydrogen gas, ammonium chloride, and potassium phosphate, with average levels reaching 248 µmol of $CH_4$. This compares with 128 µmol $CH_4$ for samples just having the $H_2$ amendment, and 64 µmol $CH_4$ for samples just having the ammonia and phosphorous compound amendment.

The combination of the hydrogen and potassium phosphate generated more methane than can be accounted for by methanogenic conversion of the added hydrogen to methane. In the methanogenic metabolism of hydrogen to methane, four moles of molecular hydrogen and 1 mole of carbon dioxide are converted into 1 mole of methane:

$$4H_2 + CO_2 \rightarrow CH_4 + 2H_2O$$

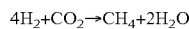

This means the 179 µmols of $H_2$ added to the sample bottles could, at most, be converted into 44.7 µmols of methane. For samples measuring peak methane production of 248 µmols, this leaves 203 µmols coming from other sources. Samples without hydrogen amendments produced about 64 µmols of methane from these coal substrates. This still leaves at least 139 µmols of methane that was generated from another source.

The source of the additional methane is believed to come from the biogenic metabolism of the coal into methane. The hydrogen and phosphorous compound amendment is believed to have stimulated the microorganisms present in the sample to metabolize the coal into methane. The stimulatory effect of the hydrogen and phosphorous amendment is not limited to enhancing the conversion of the added hydrogen gas to methane. It also includes stimulating the microorganisms to use methanogenic metabolic pathways that convert the coal substrate into methane. In additional experiments conducted with a different coal and formation water sample, hydrogen addition without an ammonium and phosphate amendment stimulated coal metabolism to methane.

Acetate Amendments

Experiments were conducted to measure the effects of acetate amendments on methane production from samples of carbonaceous materials. The carbonaceous materials used in these experiments were coal samples taken from underground coal beds at the Monarch coal site. The samples were transported under anaerobic conditions to nominal 36.5 ml serum bottles, where 1 gram samples of the coal were combined in an anaerobic glove bag with 20 mL of formation water from the same site and 0.2 mL of cell concentrate. The cell concentrate consisted of cells from about 6.6 L of formation water added to 15 mL of formation water. The headspace in the bottle above the sample was exchanged with a mixture of $N_2$ and $CO_2$ (95/5).

Figure 5:
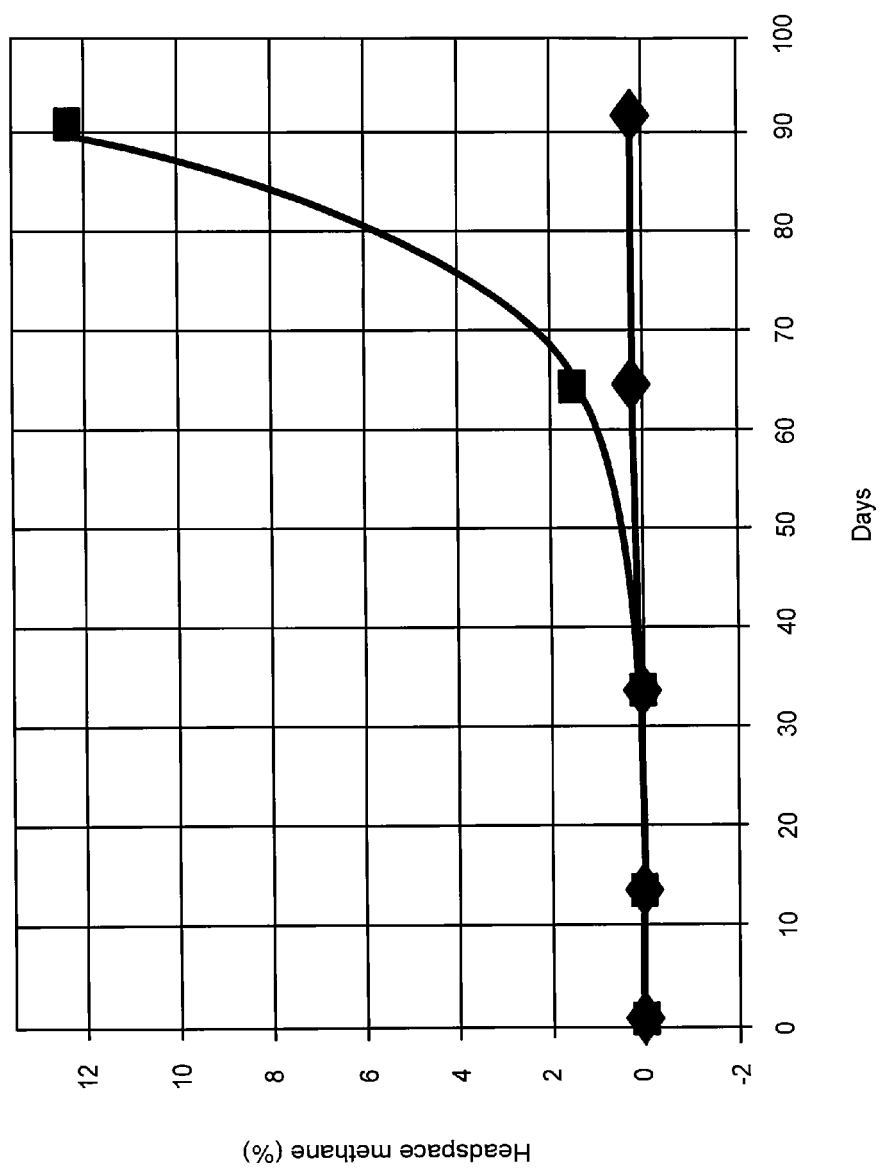
FIG. 5 is a plot that compares methane concentrations in an unamended sample with a sample treated with an acetate amendment.

In a first set of samples, the acetate amendment included adding an aqueous sodium acetate solution to the sample bottles to give the samples an 18.0 mM acetate concentration (an average measured concentration). A second set of control samples were prepared in the same manner except for lacking the acetate amendment. Methane levels (measured as a mol. % methane in the headspace of the sample bottle) were periodically measured in both the amendment and control samples over the course of 90 days. FIG. 5 shows a plot of the methane levels measured in these samples as a function of time.

Very little methane generation occurred in either the amendment or control sample during the first 50 days. But the measurement taken on day 65 shows the methane levels starting to build in the acetate amendment sample while the control sample continued to show negligible methane generation. By the 90th day, the acetate amendment sample showed rapid and significant methane generation with methane representing over 12 mol. % of the headspace in the sample bottles. Meanwhile, the control samples that lacked the acetate amendment still showed almost no methane generation after 90 days.

Figure 6:
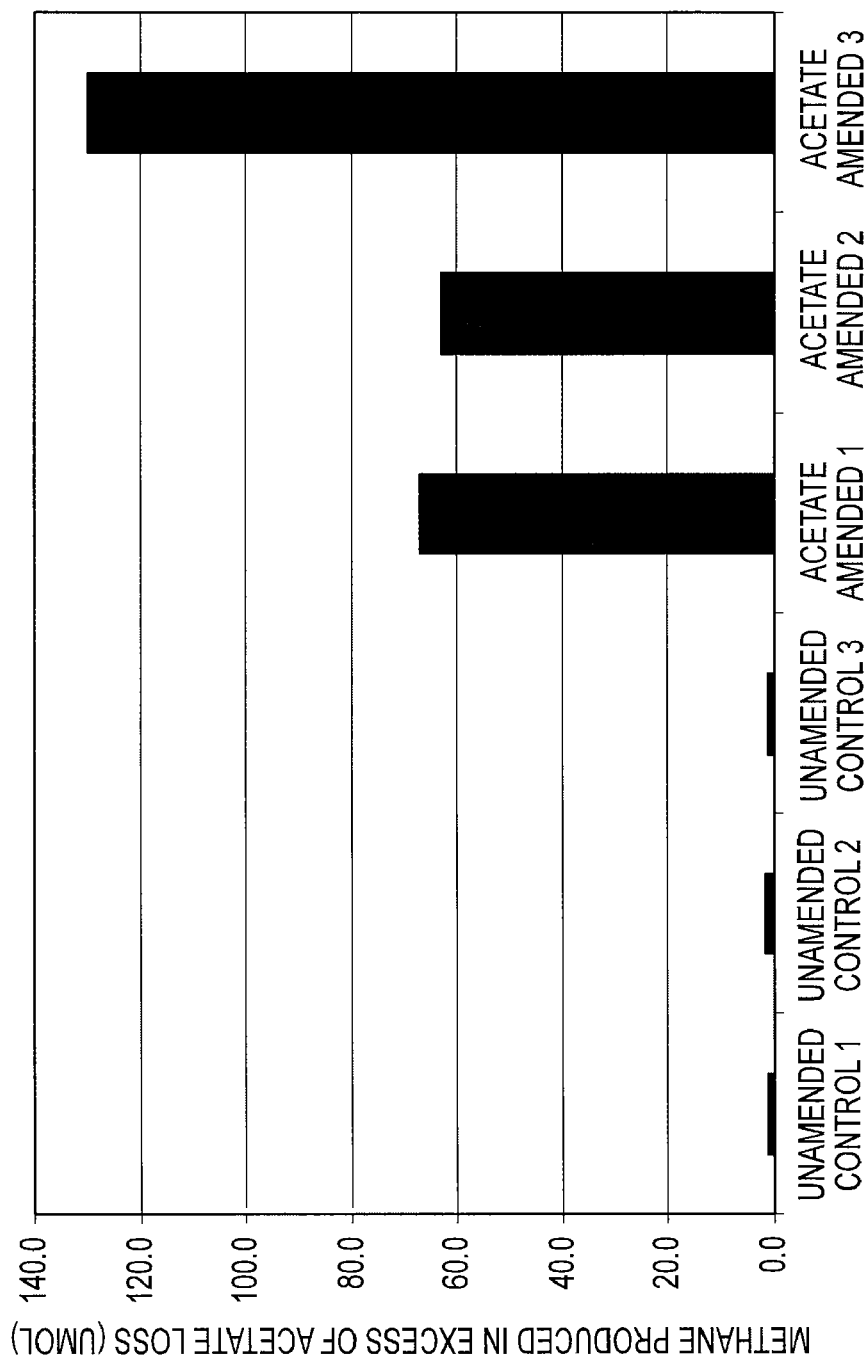
FIG. 6 is a plot showing acetate concentration over time in samples where an acetate amendment has been introduced.

FIG. 6 shows methane production in the three control samples without acetate amendments. The figure also shows methane production in acetate amended samples minus the minor amount of methane that could be accounted for by acetate utilization after 90 days. The figure also shows that the acetate amendment had a significant impact on methane generation after an activation period of about 65 days. Little change in the acetate concentration was observed either before or after the point that the methane generation rapidly increased in the acetate amended samples. These data indicate that the acetate amendment acted as an activation agent to enhance the methanogenic metabolism of the coal into methane. The data also show that the acetate activation does not occur immediately, and that a delay of several weeks to months may occur before the start of significant methanogenic activity.

Phosphorous Compound Amendments and Rollover

Rollover is a condition where the rate of biogenic methane production starts to plateau as the in situ methane concentration reaches a certain level. In many instances, the rate flattens to zero, and the methane concentration remains constant over time. The rollover point (i.e., the point where the methane concentration begins to break from a monotonically increasing state) can vary between microorganism consortia, but appears to be reached in almost all unamended samples of carbonaceous material that have been examined to date.

Figure 7:
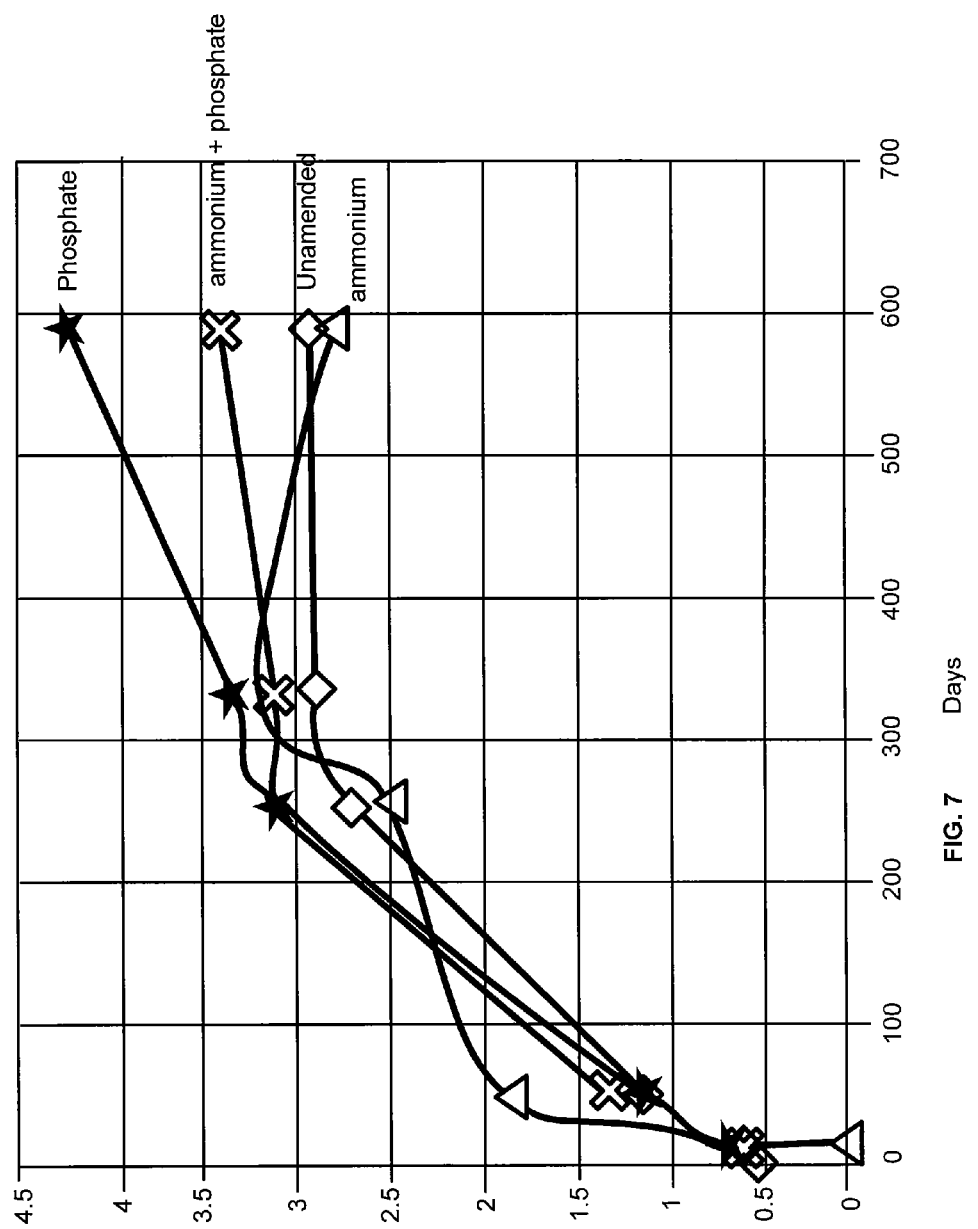
FIG. 7 is a plot of methane concentration over time in an unamended sample, and samples amended with a phosphorous compound or ammonia.

But some samples receiving minerals, metals and nutrient amendments exhibited less of a rollover effect than unamended controls. Further tests revealed that the agents responsible for reducing rollover were often phosphate compounds, such as sodium or potassium phosphate. FIG. 7 shows a plot of methane levels over time in the headspace of nominal 36.5 ml serum bottles containing amended and unamended coal samples. The plot for the unamended sample shows the rollover point occurring when the methane level in the headspace reaches between 2.5 and 3 mol. %. At these methane levels, the rate of methane production starts to decrease and the methane level remains constant at slightly under 3 mol. %.

A more volatile, but similar pattern was observed for samples treated with an ammonium amendment. In these samples, ammonium chloride was introduced to give each sample a concentration of 25 mg/L nitrogen at the start of the methane measurements. The rate of methane production in these samples was initially greater than for the unamended samples or samples with other types of amendments (including an amendment of ammonium and phosphate). In addition, the peak methane level in the ammonium samples exceeded the peak plateau levels in the unamended samples. By about day 600 the methane levels in the samples were about the same as those measured in the unamended samples.

The samples treated with an amendment that included a phosphorous compound (i.e., potassium phosphate) all appeared to breakthrough the plateau methane level observed in the samples that were prone to rollover. As FIG. 7 shows, samples treated with a pure 5 mg/L potassium phosphate amendment had a methane level of about 4.3 mol. % after 600 days, or about 43% higher than samples without phosphate. Amendments with ammonium chloride and phosphate did not result in substantial increases.

Figure 8:
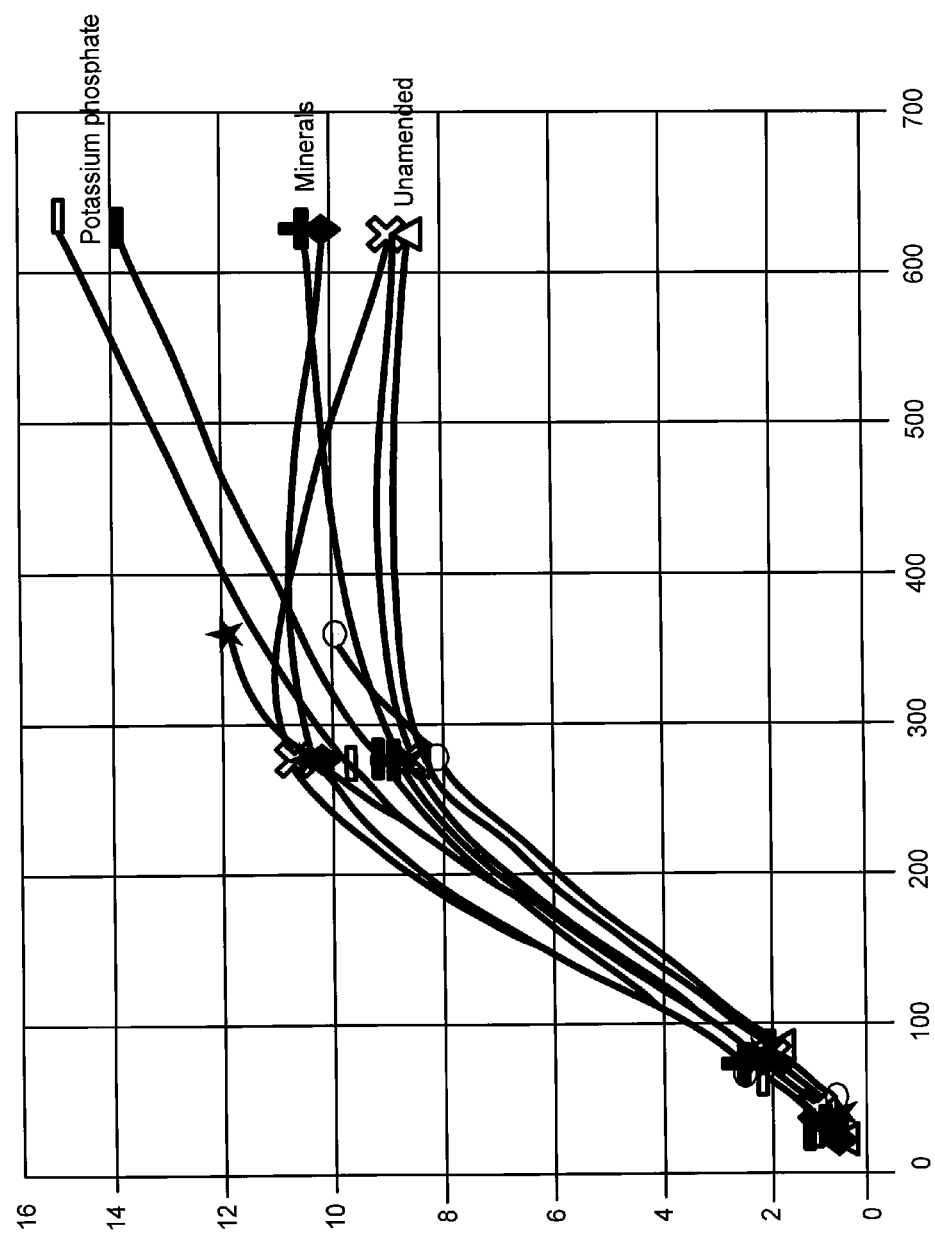
FIG. 8 is a plot of methane concentration over time in an unamended sample, and samples amended with a phosphorous compound or a mineral composition

FIG. 8 shows another plot of methane concentration over time for samples with and without phosphorous compound amendments. Similar to the plot in FIG. 7, this plot shows samples that were not treated with a phosphorous amendment (i.e., a potassium phosphate amendment) reached a rollover point beyond which the methane concentration did not increase. In contrast, no plateau was observed in the methane concentration of two sets of samples that were treated with a phosphate amendment. At the end of just over 600 days, the phosphate containing samples had significantly higher methane levels than samples treated with a minerals amendment or the samples that were unamended.

FIGS. 7 and 8 indicate that phosphorous compounds such as potassium phosphate can extend methanogenesis supported by complex hydrocarbons. Thus, the introduction of a phosphorous compound amendment to microorganisms in a geologic formation may stimulate the microorganisms to continue to produce methane.

Single and Multiple Nutrient Amendments

Figure 9:
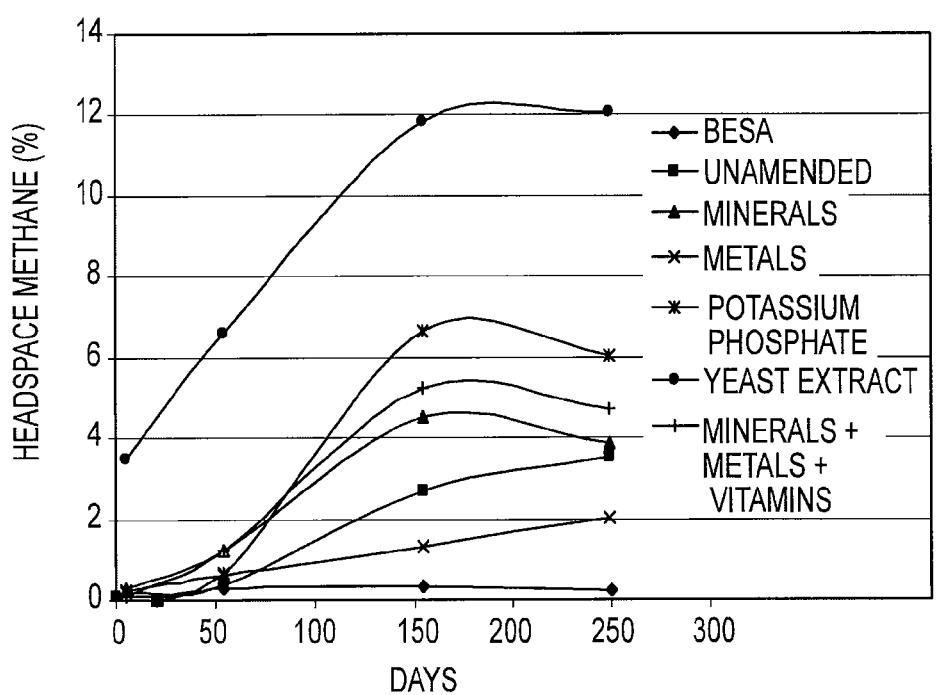
FIG. 9 is another graph of measured methane concentration over time in samples of carbonaceous materials treated with various amendments.

Additional experiments indicate that single nutritional amendments can stimulate methanogenesis in many cases to levels greater than observed with the addition of more complex amendments. FIG. 9 shows a graph of measured methane concentration over time in samples of carbonaceous material (i.e., coal from the Powder River Basin) treated with single and multiple nutrient amendments. These amendments included (1) a single phosphorous compound amendment (potassium phosphate), (2) a single yeast extract amendment, (3) a metals only amendment, (4) a minerals only amendment, and (5) a minerals, metals, and vitamins (MMV) amendment. Two comparative groups were also measured: (1) Samples of the Power River Basin coal to which no amendments were added (unamended), and (2) Samples of the PRB coal to which bromoethanesulfonic acid (BESA), a known methanogen-specific inhibitor, was added.

Similar to the hydrogen plus phosphorous and acetate experiments, the samples were prepared under anaerobic conditions in nominal 36.5 ml serum bottles, where 5 grams samples of the coal were combined in an anaerobic glove bag with 15 mL of formation water from the same site. The headspace in the bottle above the sample was exchanged with helium.

The amendments were added to the sample bottles until a target concentration of the amendment was reached. For the phosphorous only amendment, potassium phosphate was added to the sample bottles until a concentration of 5 mg/L was reached. For the yeast extract only amended, Difco® yeast extract from Becton Dickinson and Company was added to the sample bottles until a concentration of about 500 mg/L was reached. For the metals only amendment, an aqueous solution of the metal salts listed in Table 1 below was added to the sample bottles until the listed sample bottle concentrations were reached:

TABLE 1

Components of the Metals Amendment

| Component | Stock Concentration g/L | Sample Bottle Concentration g/L |
|---|---|---|
| Nitrilotriacetic acid Adjust pH to 6 with KOH | 0.2 | .0067 |
| $MnSO_4 \cdot H_2O$ | 0.1 | .0033 |
| $Fe(NH_4)2(SO_4)2 \cdot 6H_2O$ | 0.08 | .0027 |
| $CoCl_2 \cdot 6H_2O$ | 0.02 | .00067 |
| $ZnSO_4 \cdot 7H_2O$ | 0.02 | .00067 |
| $CuCl_2 \cdot 2H_2O$ | 0.002 | .000067 |
| $NiCl_2 \cdot 6H_2O$ | 0.002 | .000067 |
| $Na_2MoO_4 \cdot 2H_2O$ | 0.002 | .000067 |
| $Na_2SeO_4$ | 0.002 | .000067 |
| $Na_2WO_4$ | 0.002 | .000067 |

For the minerals only amendment, an aqueous solution of minerals listed in Table 2 below was added to the sample bottles until the listed sample bottle concentrations were reached:

TABLE 2

Components of the Minerals Amendment

| Component | Stock Concentration g/L | Sample Bottle Concentration g/L |
|---|---|---|
| NaCl | 80 | 0.2 |
| $NH_4Cl$ | 100 | 0.25 |
| KCl | 10 | 0.025 |
| $KH_2PO_4$ | 10 | 0.025 |
| $MgCl_2 \cdot 6H_2O$ | 20 | 0.05 |
| $CaCl_2 \cdot 2H_2O$ | 4 | 0.1 |

For the minerals, metals and vitamins amendment (MMV), aqueous solutions of the minerals and metals listed above where added to a solution of vitamins listed in Table 3 below. The vitamins were present in the sample bottles at the listed concentrations.

TABLE 3

Components of the Vitamin Amendment

| Component | Sample Bottle Concentration mg/L |
|---|---|
| Pyridoxine-HCl | 0.1 |
| Thiamine-HCl | 0.05 |
| Riboflavin | 0.05 |
| Calcium pantothenate | 0.05 |
| Thioctic acid | 0.05 |
| p-Aminobenzoic acid | 0.05 |
| Nicotinic acid | 0.05 |
| Vitamin $B_{12}$ | 0.05 |
| MESA | 0.05 |
| Biotin | 0.02 |
| Folic acid | 0.02 |

Finally, for the samples used in the comparative example where methane production from methanogenesis was inhibited, BESA was added to the sample bottles until it reached a concentration of about 10 mM.

Methane production from the samples were measured and plotted as the percentage of methane in the headspace above the liquid in the serum bottle. Three sample bottles were prepared for each amendment, and the methane concentrations were measured in triplicate and averaged.

As the graph shows in FIG. 9, methane did not accumulate in the BESA controls, indicating that the source of methane in the unamended and nutrient supplemented incubations was methanogenesis. Surprisingly, rates and yields of methanogenesis were highest within incubations supplemented with a single nutritional amendment (i.e., yeast extract and potassium phosphate) relative to incubations amended with mixtures of multiple nutrients. The minerals mixture, and the mixture of minerals, metals, and vitamins (both mixtures contain phosphate) also stimulated methanogenesis relative to unamended incubations but not to the same extent as potassium phosphate alone.

Methane production appeared to be inhibited in samples amended with a metals mixture alone, possibly due to metal toxicity. This was not expected since the concentrations used for these experiments are commonly added to microbiological media for culturing microorganisms. Metal toxicity to methanogenesis has also been observed in some samples even after reducing the concentration of metals by ten-fold. Overall, the data acquired for this sample indicate that conventional nutritional supplements were either less effective relative to phosphorous compounds and yeast extracts alone, or were inhibitory.

Phosphorous Compound Amendments in Oil Samples

Produced water and oil samples were collected directly from well heads after passing produced fluids through a portable anaerobic and disinfected oil-water separator. Strict anoxic techniques were used. The water samples were maintained at field temperature prior to use in experiments.

Twenty mls of produced water and 0.1 ml of oil were distributed into sterile 36.5 ml serum bottles contained within a disinfected anaerobic glove bag. The anaerobic glove bag contained a filtration apparatus for removing airborne microbial contaminants. The final headspace of the incubations was $He/CO_2$ at a mixture that resulted in a pH within 0.3 pH units of produced water pH (6.7) measurements. Incubation temperature was 45° C., the approximate in-situ temperature. Incubation period prior to headspace gas analysis was 14 days. The samples were prepared with the following amendments: (1) Sodium phosphate. Final bottle concentration –0.5 mg/L as Phosphorous; (2) Minerals (100× less the stock concentration in Table 2); (3) Metals (300× less the stock concentration in Table 1); (4) Minerals+Metals+Yeast extract (25 mg/L); (5) Minerals+Metals+Vitamins (100× less the stock concentration in appendix 1)+Yeast extract (25 mg/L). In addition, two comparative experiments were run for: (1) Unamended samples; and (2) Samples treated with BESA (10 mM).

The experimental bottles were placed into a heated water bath maintained at the field temperature during gas analysis to avoid temperature fluctuations. Gas samples were periodically obtained for methane and carbon dioxide analysis using a gas chromatograph equipped with a thermal conductivity detector. The methane measurements, expressed as the percentage of methane in the headspace above the sample bottles, were plotted in FIG. 10.

Figure 10:
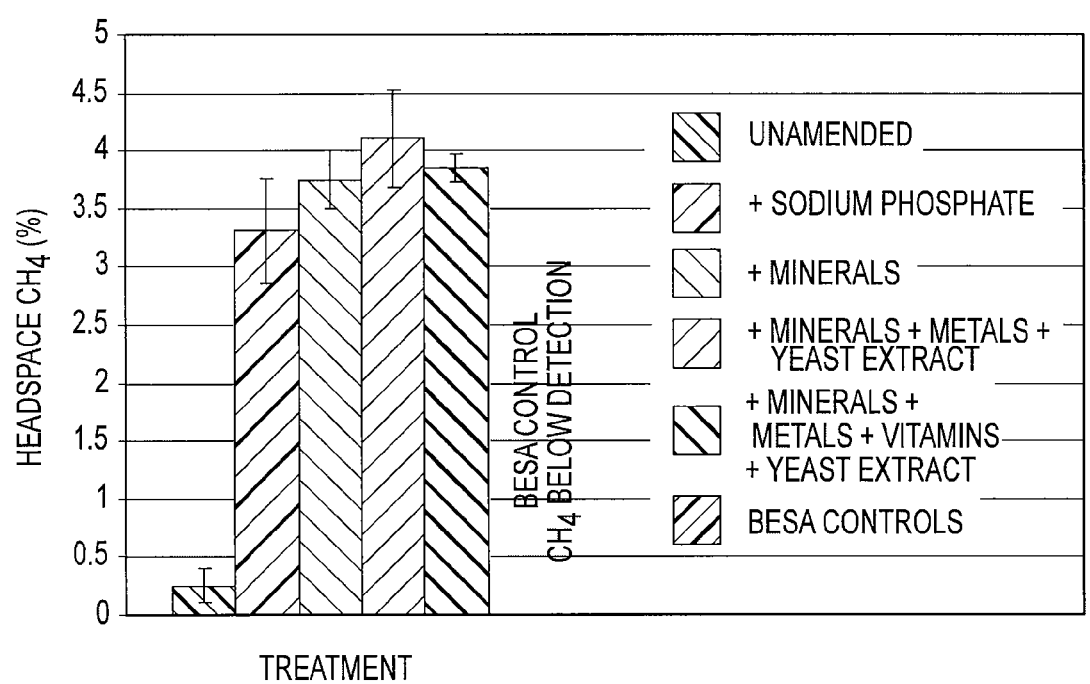
FIG. 10 is another plot of measured methane concentrations for various amendments made to samples of carbonaceous materials.

As FIG. 10 shows, methanogenesis was below detection in the BESA inhibited controls, relatively slow in unamended controls, and substantially increased in nutrient amended samples. The addition of phosphate (as sodium phosphate) alone resulted in comparable stimulation relative to more complex nutrient mixtures including the minerals+metals+vitamins+YE mixture which contains phosphate and twenty five additional nutrient elements. These data indicate that phosphate was active in stimulating increased methanogenesis, and that the other constituents of the mixtures were as stimulatory relative to phosphate alone. The error bars in FIG. 10 represent the standard deviation of the measurements.

In order to confirm that the oil results were not unique to the specific oil substrate used (which was taken from a field in Texas), the experiments were re-run with oil from a different field in Montana. The sample collection, experimental workups and analytical measurements were the same as described above, and the results were plotted in FIG. 11A.

Figure 11A:
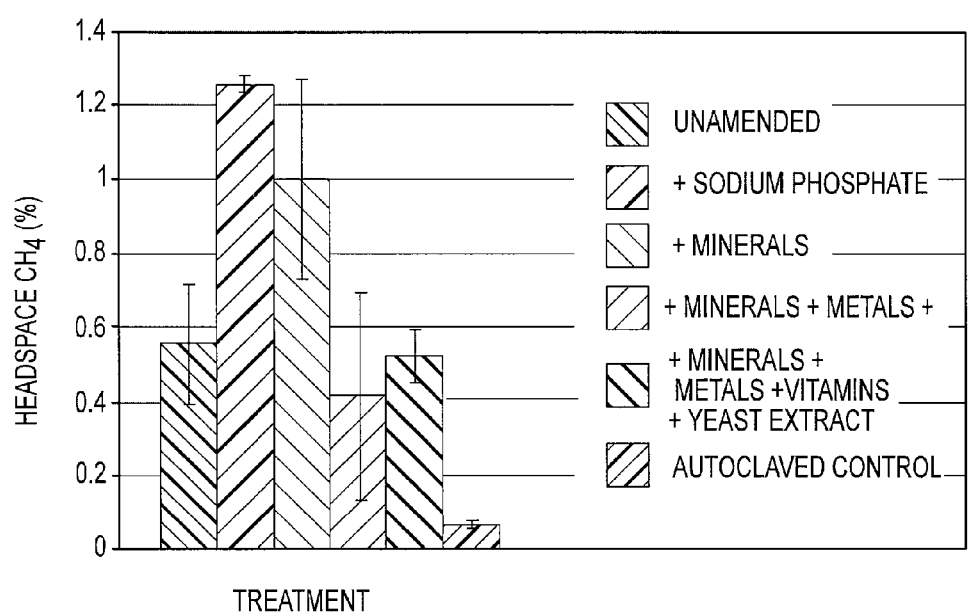
FIGS. 11A-B are additional plots of measured methane and acetate concentrations for various amendments made to samples of carbonaceous materials.

FIG. 11A shows that the highest rates of methanogenesis in samples from a second oil field were detected in incubations amended with sodium phosphate and the minerals solution. As observed in cases 1 and 2, sodium phosphate addition alone resulted in comparable stimulation relative to the minerals mixture which contains additional nutrient elements (ammonium, calcium, potassium, and magnesium). The addition of nutrient mixtures containing metals reduced methanogenic activity relative to the minerals only amendment, presumably due to metal toxicity despite decreasing the metals concentration by 10× relative to concentrations commonly used in microbiological media.

Figure 11B:
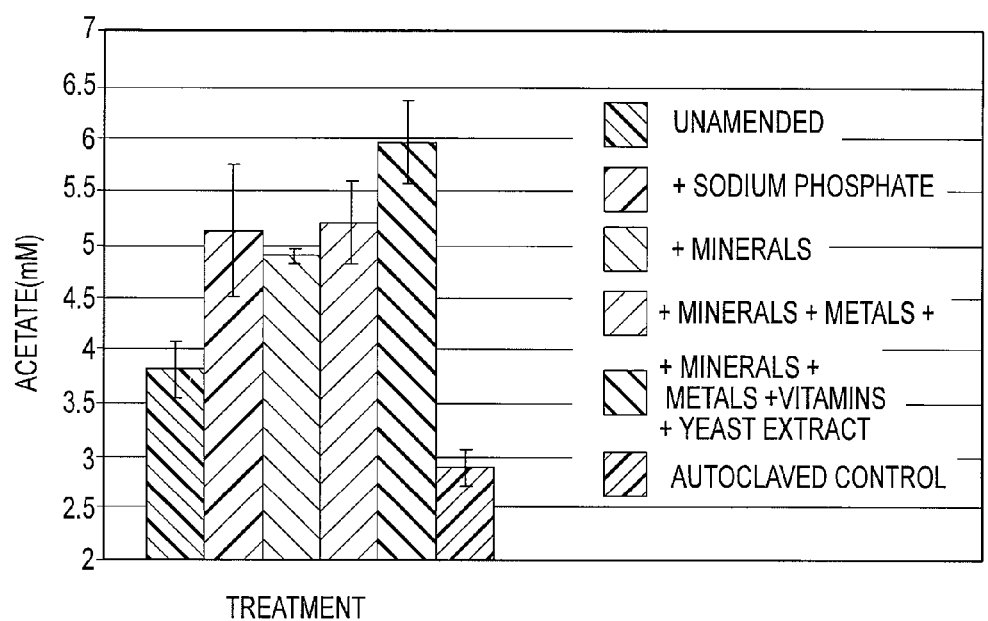

Acetate measurements were also taken on the samples, and the results plotted in FIG. 11B. As the bar graph in FIG. 11B shows, all nutrient additives, including sodium phosphate alone, stimulated acetate production relative to the unamended controls. These data indicate that sodium phosphate is a stimulative nutritional amendment that stimulates both methanogenesis and upstream metabolism responsible for acetate production. Nutrient mixtures did not stimulate methanogenesis relative to the unamended controls. The error bars in FIGS. 11A&B represent the standard deviation of the measurements.

Identification and Cultivation of Methanogenic Microorganism Consortia

Methanogenic consortia have been detected from a diverse array of subsurface geologic formations, including coal seams in the Powder River Basin, oil reservoirs, Antrim shale, and siltstone formations in Montana. The detection of methanogenic microorganisms over a wide range of geologic formation environments indicate a wide prevalence of native microorganism consortia with methanogenic activity. In some instances, however, methanogenic microorganisms were detected in formation waters but not solid samples of the formation. This is presumably due to inadequate fracture and/or pore spaces in the solids, but may also indicate differences in the types of microorganisms that are favored in each medium.

Figure 12:
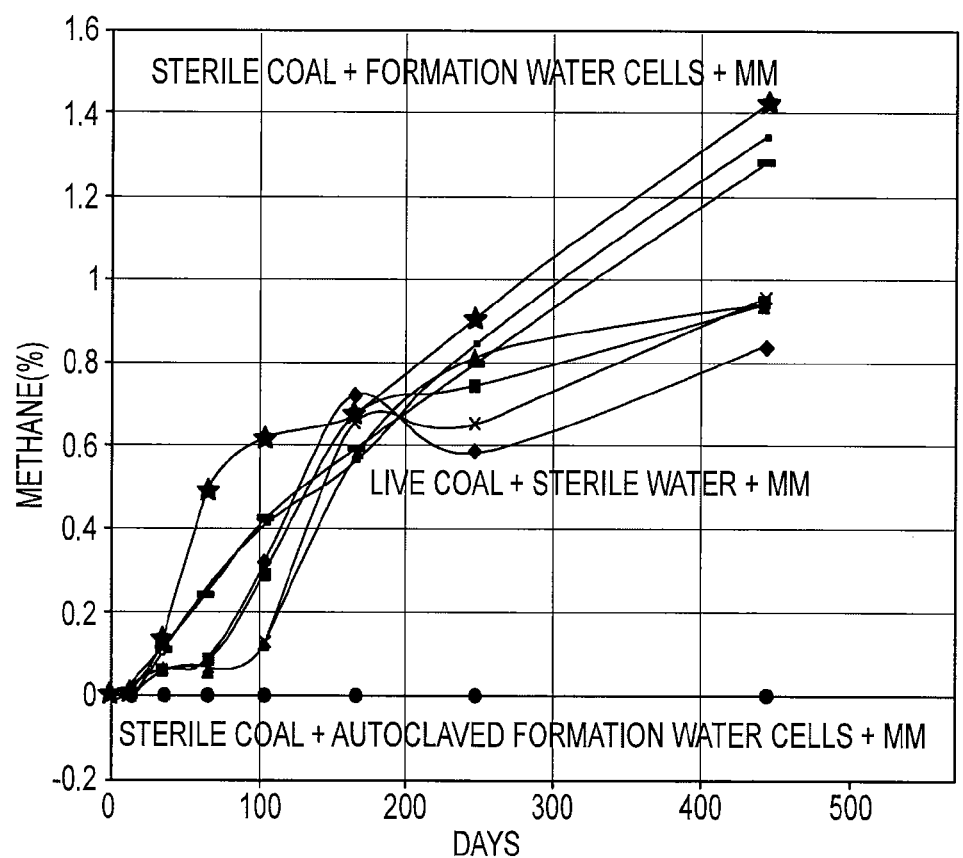
FIG. 12 is an additional plot of the measured methane concentrations for various amendments made to samples of carbonaceous materials.

Experiments were conducted to compare methanogenic activity from microorganism consortium in formation water and solid coal substrates. FIG. 12 plots the change in the methane concentration (measured as the percentage of methane in the headspace above the liquid in the sample bottle) over time for consortium that originated with the formation water and solid coal. All samples were obtained from the Monarch coal seam in the Powder River Basin of Wyoming.

In one set of samples, the formation water was sterilized by autoclaving while the solid coal remained "live" to preserve any microorganisms in the coal. In another set of samples, the coal was sterilized by autoclaving, while microorganisms in the formation water were preserved. Finally, as a comparative example, both the coal and formation water were sterilized to monitor how much, if any, came from non-biological activity. In all samples also included a nutrient amendment of minerals and metals similar to those described in Tables 1 and 2 above.

As FIG. 12 shows, methane production was observed when a live microorganism consortium from either the formation water or the coal was present in the sample. The lack of methane production in the completely sterilized control sample indicated that the methane production in the live samples was due to methanogenic microorganisms. and not, for example, desorption of methane that might have been stored in interstitial spaces of the coal sample. The data also show that over a period of about 250 days, methanogenesis from microorganism consortiums originating either from the formation water or the coal progressed at similar rates. Over longer periods (i.e., 450 days) it appears the consortiums from the formation water produce more methane than those from the coal.

With the discovery that methanogenic consortia are commonly present in formation waters, a significant research effort, both laboratory and field oriented, was directed at identify methodologies for enhancing their activities in-situ. To this end, methanogenic consortia capable of rapid methanogenesis on coal from the Powder River Basin have been obtained using an enrichment procedure wherein a small volume of an active consortium is added to a "sterile" slurry bottle (in this case, autoclaved Tongue River coal and filter sterilized Tongue River formation water). The consortium is allowed to grow and metabolize, then the dilution series is repeated. This enrichment procedure appears to favor the growth of microorganisms more capable of metabolizing coal to methane.

Figure 13:
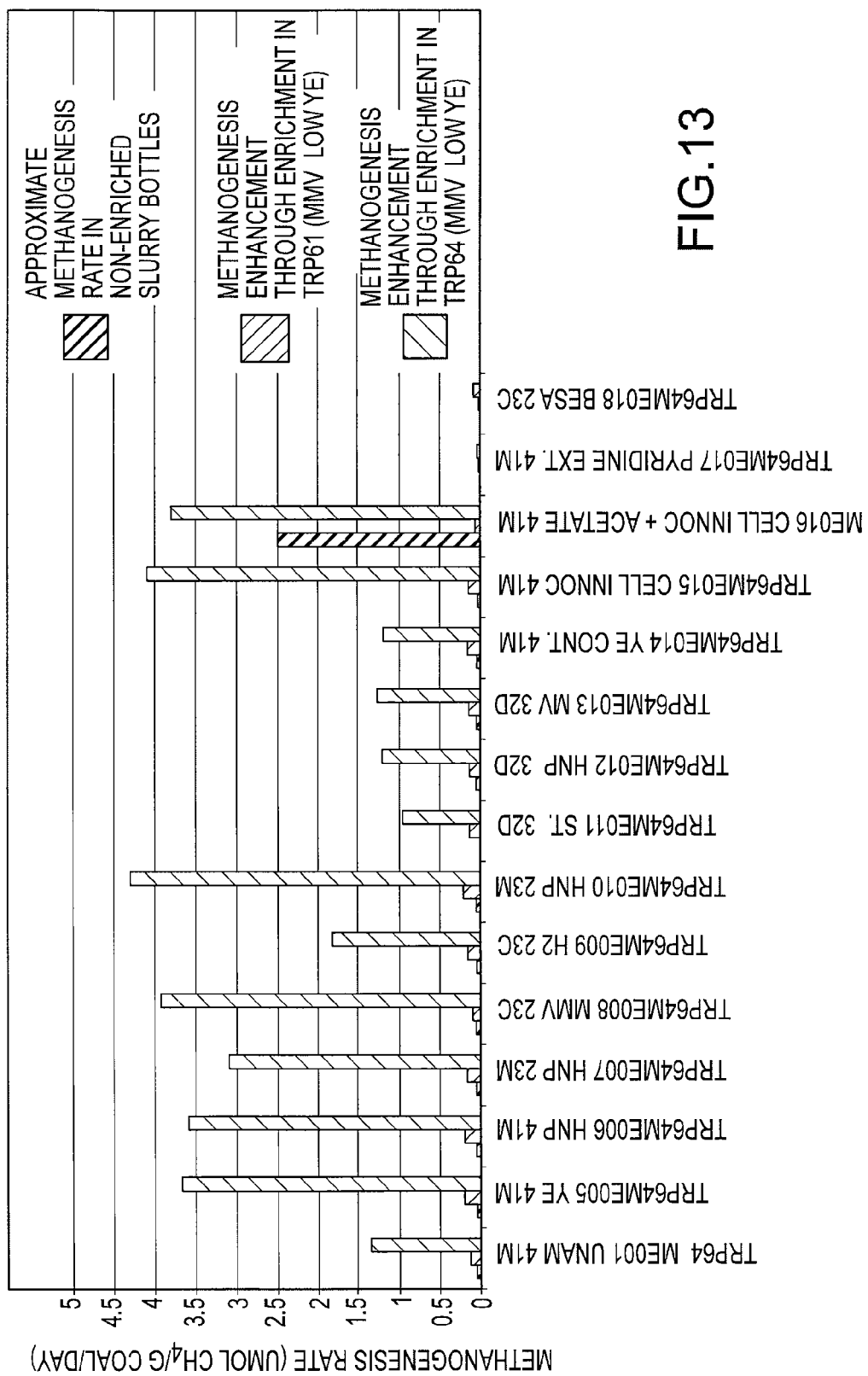
FIG. 13 is a bar graph showing methanogenesis rates in amended and unamended samples of carbonaceous materials.

FIG. 13 shows the results where part of an original "parent" consortium is transferred to a second sterile slurry bottle for cultivation, and then part of the second consortium is transferred to a third sterile slurry bottle. The graph in FIG. 13 shows 16 sets of three bars, with the leftmost bar showing the rate of methane production from the parent consortium, the middle bar indicating the methane production rate after the first transfer, and the rightmost bar showing the methane production rate after the second transfer. The data show that methanogenic rates increased substantially after the first transfer (middle bars) and again after the second transfer (rightmost bars). Very rapid methanogenesis was observed after the second transfer with rates 57 times greater on average relative to the parent samples (leftmost bars). The two exceptions to the trend were the last two sample sets on the far right of FIG. 13. These were cases in which methanogenesis was inhibited in the parental bottles intentionally with BESA and unintentionally in bottles that received solvent (pyridine) extracts of coal. In these samples, the predominant end-product of metabolism was acetic acid indicating that a consortium comprised primarily of microorganisms involved in upstream hydrocarbon metabolism to acetate was obtained.

The methanogenic rates on the far left set of activity in the initial non-enriched samples were prepared with three different coals under a myriad of conditions including unamended samples, and samples amended with chemical additives including several nutrients. Highly methanogenic consortiums appeared to develop independently of the water and coal source of the initial inoculum source or whether chemical amendments were added to the initial inoculum source.

This enrichment process generated methanogenic consortia capable of supporting methanogenesis on coal substrate at rates in great excess relative to what would be anticipated. Another surprising result was that the presence of hydrogen gas or acetate in the parental inoculum sources did not impede the development of highly methanogenic consortia including microorganisms involved in upstream hydrocarbon metabolism. Furthermore, results showed that very dilute inoculum doses are effective (up to 65,000× dilutions have been successful) and that methanogenic consortia remain capable of rapid methanogenesis well after methanogenesis subsides (data not shown).

Field Test Data for Stimulating Methanogensis

The laboratory experiments produced a number of discoveries including: 1) methanogenic consortia have been detected in formation waters of many subsurface formations; 2) highly effective methanogenic consortia can be obtained by transporting members of an active consortium from one site to another; 3) these highly effective consortia can be derived from parental samples containing "activated" methanogenic consortia independently of whether nutritional amendments, hydrogen, acetate, and combinations thereof aided the activation; and 4) phosphorous compound and yeast extract amendments alone are, in some instances, more effective nutrient stimulants for methanogenic microorganisms than more complex, multi-nutrient mixtures. It was also observed that very small inoculum doses can be effective and that highly effective methanogenic consortia can persist well after methanogenesis subsides. These laboratory findings were then tested in coal seams of the Powder River Basin.

Field Test Data

Figure 14A:
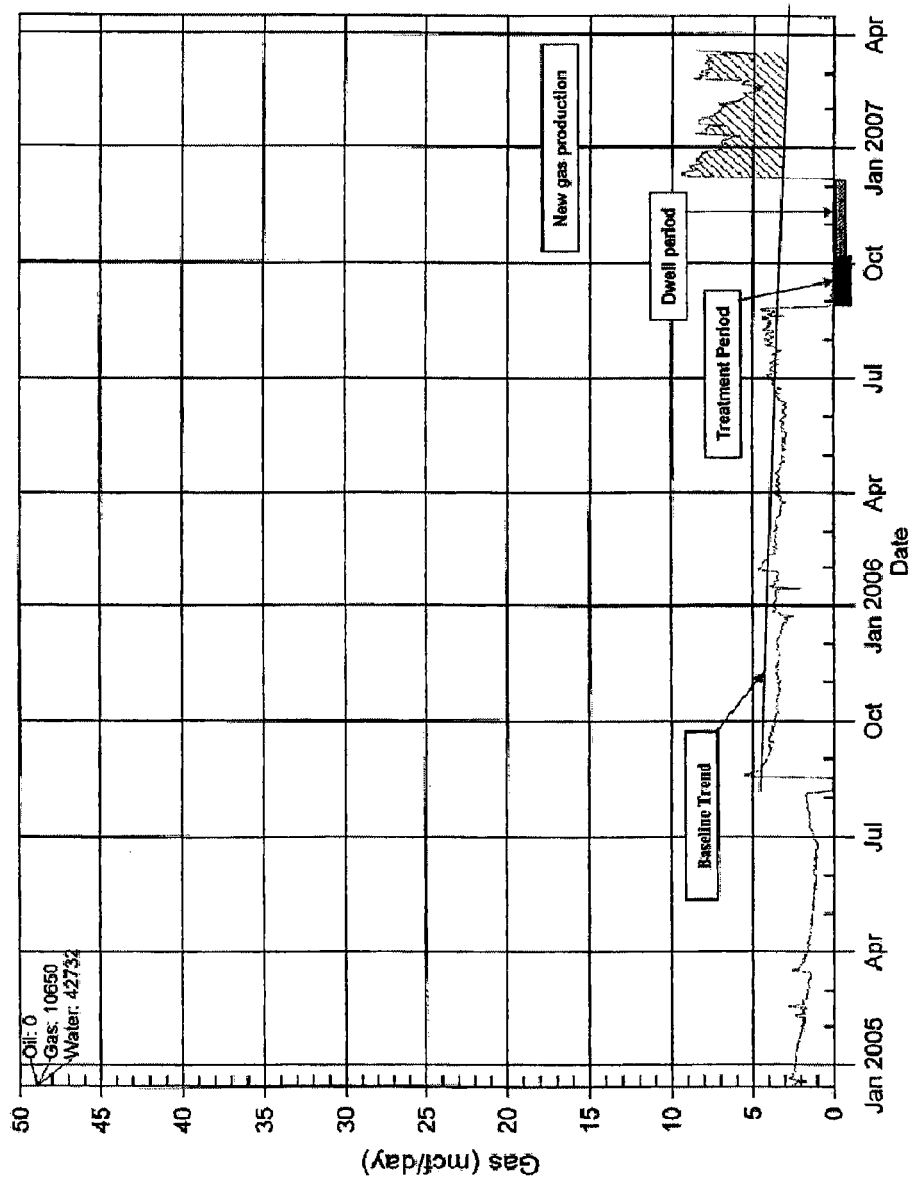
FIGS. 14A-B are graphs of measurements of natural gas production over time from a coal formation before and after an amendment of phosphate was introduced to the formation.
Figure 14B:
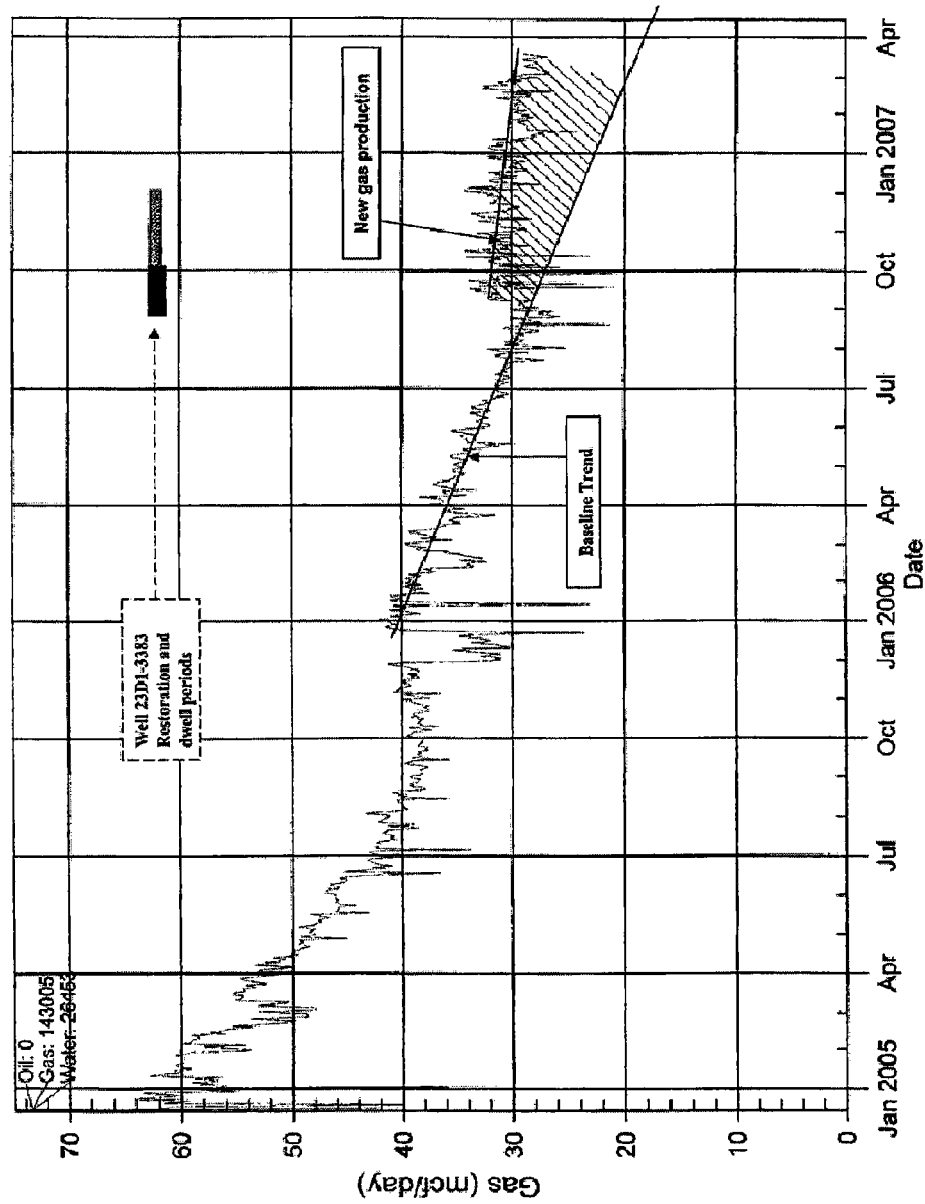

FIGS. 14A-B show graphs of measurements of methane gas production over time from a coal formation in Wyoming's Powder River Basin before and after an amendment of phosphate and filtered water was introduced to the formation. As shown in the left two-thirds of the graph in FIG. 14A, a baseline trend measurement of gas production from the well that was taken over a period of about 1.75 years showed a production rate that almost never went above 5 mcf/day (1 mcf=one thousand cubic feet).

The gas well was then treated with an amendment of phosphate and filtered water for about 1.2 months (i.e., late August to early October). The amendment included the introduction of an aqueous solution of $9.5 \times 10^{-5}$ M potassium phosphate to an underground natural gas formation at a rate of about 14,400 L/day for each day of the treatment period. Following the treatment period with the phosphorous amendment, the gas well was sealed for a period of about 2 months (i.e., early October to early December) before the measurements of gas were measured during the post-amendment period (the dwell period).

Following the treatment and dwell periods, FIG. 14 A shows the natural gas production rate jumping to over 9 mcf/day, which was about double the average production rate during the baseline period. Moreover, while the data showed fluctuations in the gas production rate during the December to March post-treatment period, the rate almost never dipped below 5 mcf/day. This data clearly shows that the phosphorous amendment increased the production of natural gas in the formation.

FIG. 14B shows another example of a phosphorous amendment increasing methane production from an underground formation that produces natural gas. The left three-fourths of the graph clearly show a baseline trend in the natural gas product rate trending downwards from about 60 mcf/day to 30 mcf/day over the period of about 1.75 years. Then the same phosphorous amendment as described for FIG. 14A was added to the formation for a 1.2 month period (i.e., late August to early October) followed by an approximately 2 month dwell period.

The graph clearly shows a jump in the natural gas product rate following the treatment and dwell periods and, in addition, shows the increase almost immediately followed the introduction of the phosphorous amendment. Thus, FIGS. 14A and 14B show that a phosphorous amendment can increase methane production in low-level producing (FIG. 14A) and declining (FIG. 14B) natural gas formation environments.

Figure 15A:
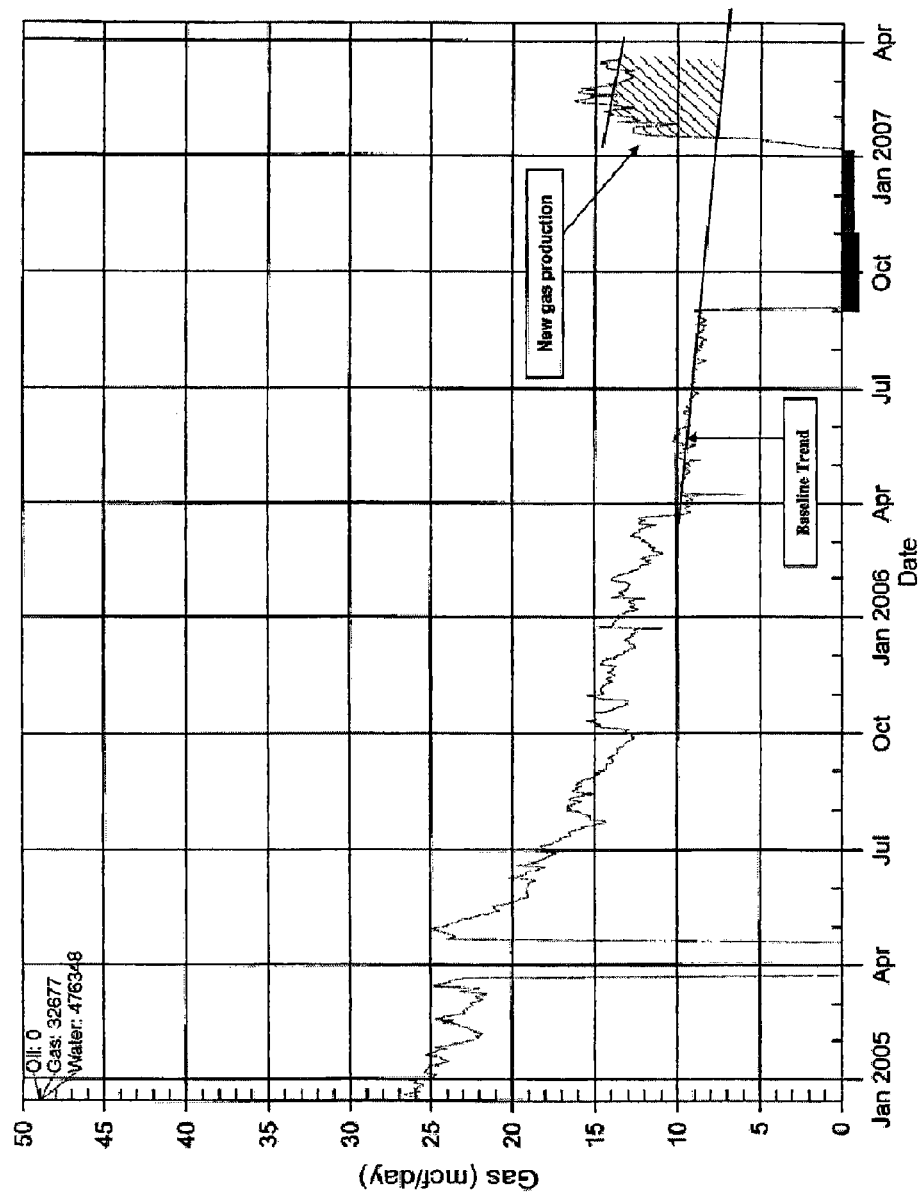
FIGS. 15A-C are graphs of measurements of natural gas production over time from a coal formation before and after the introduction of a consortium of microorganisms that were found to be active, or activated in a different formation.
Figure 15B:
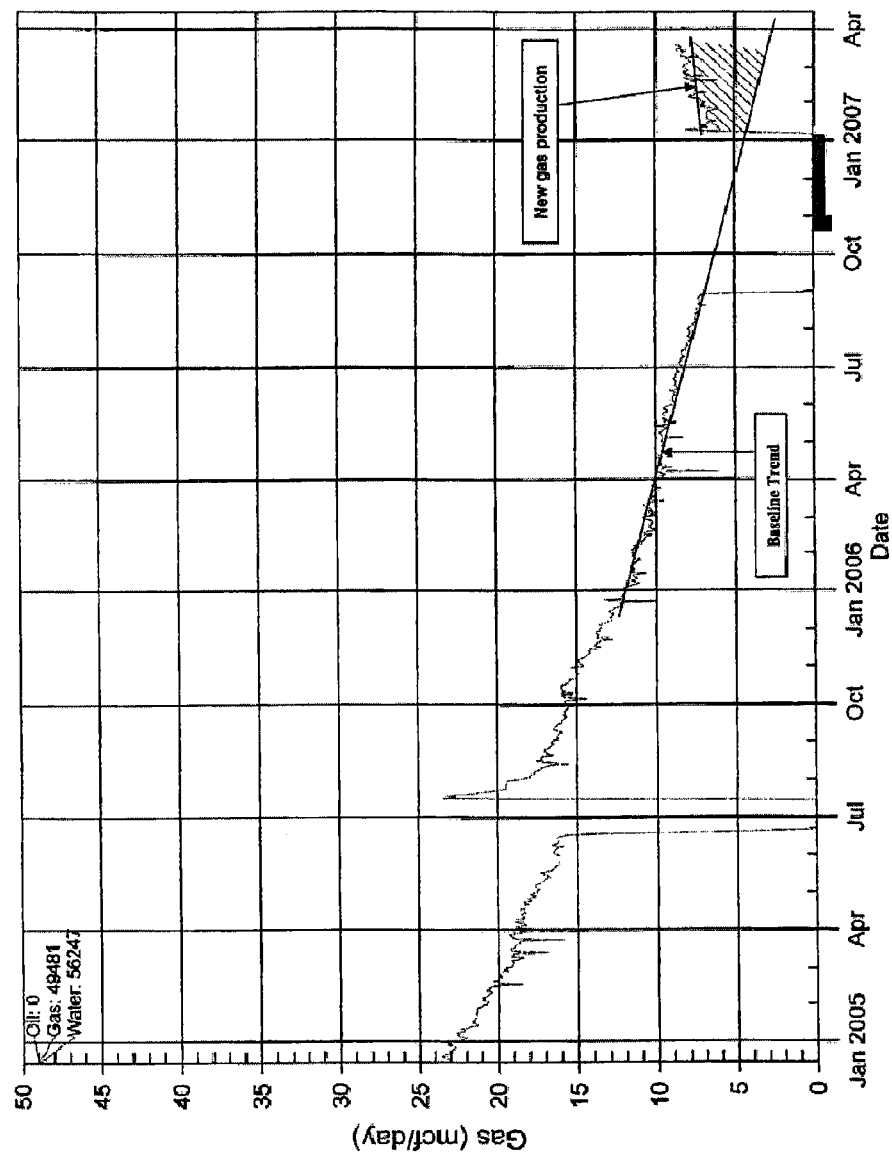

Referring now to FIGS. 15A and 15B, more measurements of methane production rates from a methane generating underground formation are plotted before and after an amendment is introduced to the formation. In these field tests, the amendment was "live" water that included a microorganism consortium that was taken from a different formation where biogenic methane production had been observed.

As shown in the left two-thirds of the graph in FIG. 15A, a baseline trend measurement of gas production from the well that was taken over a period of about 1.75 years showed a declining production rate going from about 25 mcf/day to less than 10 mcf/day. The gas well was then treated with an amendment of methanogenic microorganisms in water for about 2 months (i.e., September and October). The amendment included the introduction of an aqueous solution of the microorganisms to an underground natural gas formation at a rate of about 29,400 L/day for each day of the treatment period. The concentration of the microorganisms were, on average, about $2.3 \times 10^6$ cells/ml. Following the treatment period with the microorganism amendment, the gas well was sealed for a period of a little more than 2 months (i.e., November to early January) before the measurements of gas were measured during the post-amendment period (the dwell period).

The post-amendment period on the righthand side of FIG. 15A clearly shows an increase in natural gas production following the dwell period. The methane production rate jumped from about 9 mcf/day immediately before the treatment period to about 13 mcf/day after the period. Moreover, the production rate peaked at about 16 mcf/day about 1.5 months after the end of the dwell period.

A similar effect was seen in FIG. 15B where the baseline trend of decreasing natural gas production was reversed by the addition of a "live" water amendment. In this formation, the baseline trend in methane production was a rate decline from about 23 mcf/day to about 7 mcf/day over the course of 1.75 years. (Note: In June of the first recorded year, the pump installed at the well was changed, which may account for the temporary gas production perturbation between June and July of that year.) Then following a 2 month amendment with live water and a little more than 2 month dwell period with the same treatment conditions as described for FIG. 15A, the methane production rate reversed and started to increase.

FIG. 15B clearly shows that the addition of a methanogenic microorganism consortium can increase natural gas production of a formation.

Figure 15C:
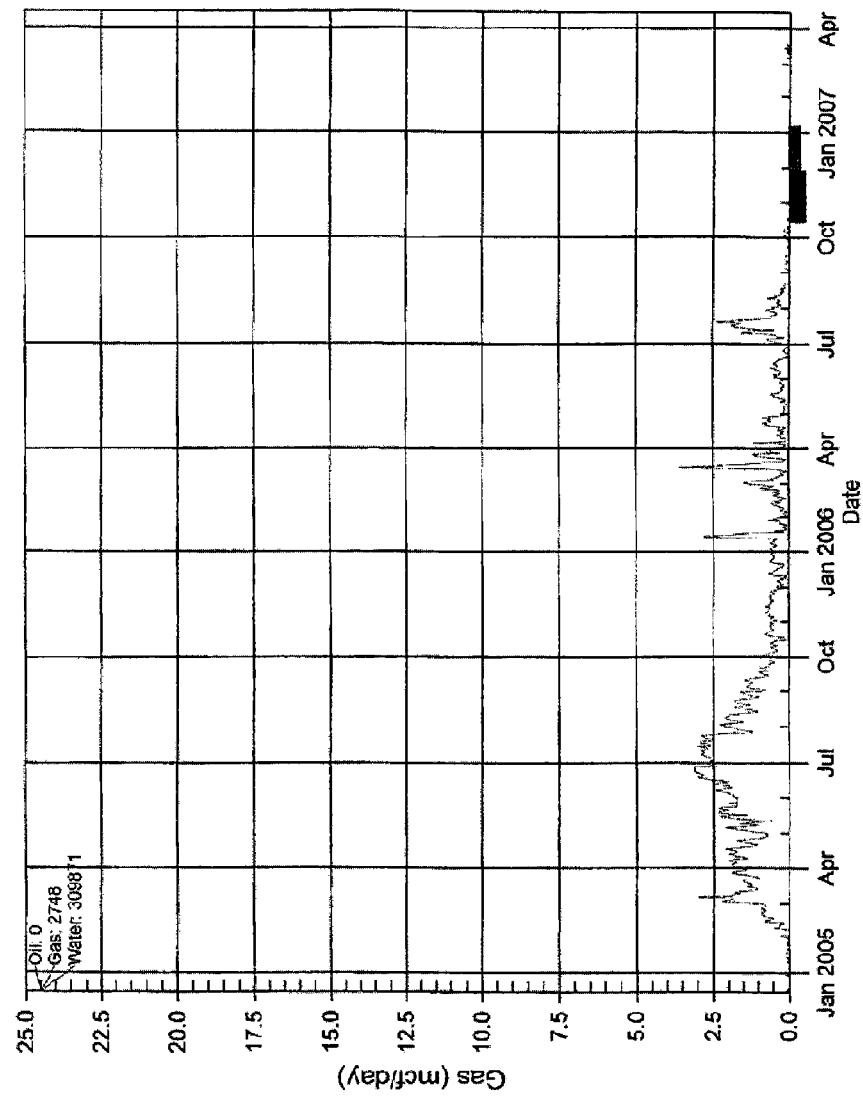

Not all the field tests with live water amendments showed an increase in the natural gas production rate. FIG. 15C shows that a live water amendment from a well with a relatively low baseline production rate (e.g., about 1-2 mcf/day) did not increase the production rate.

Figure 16:
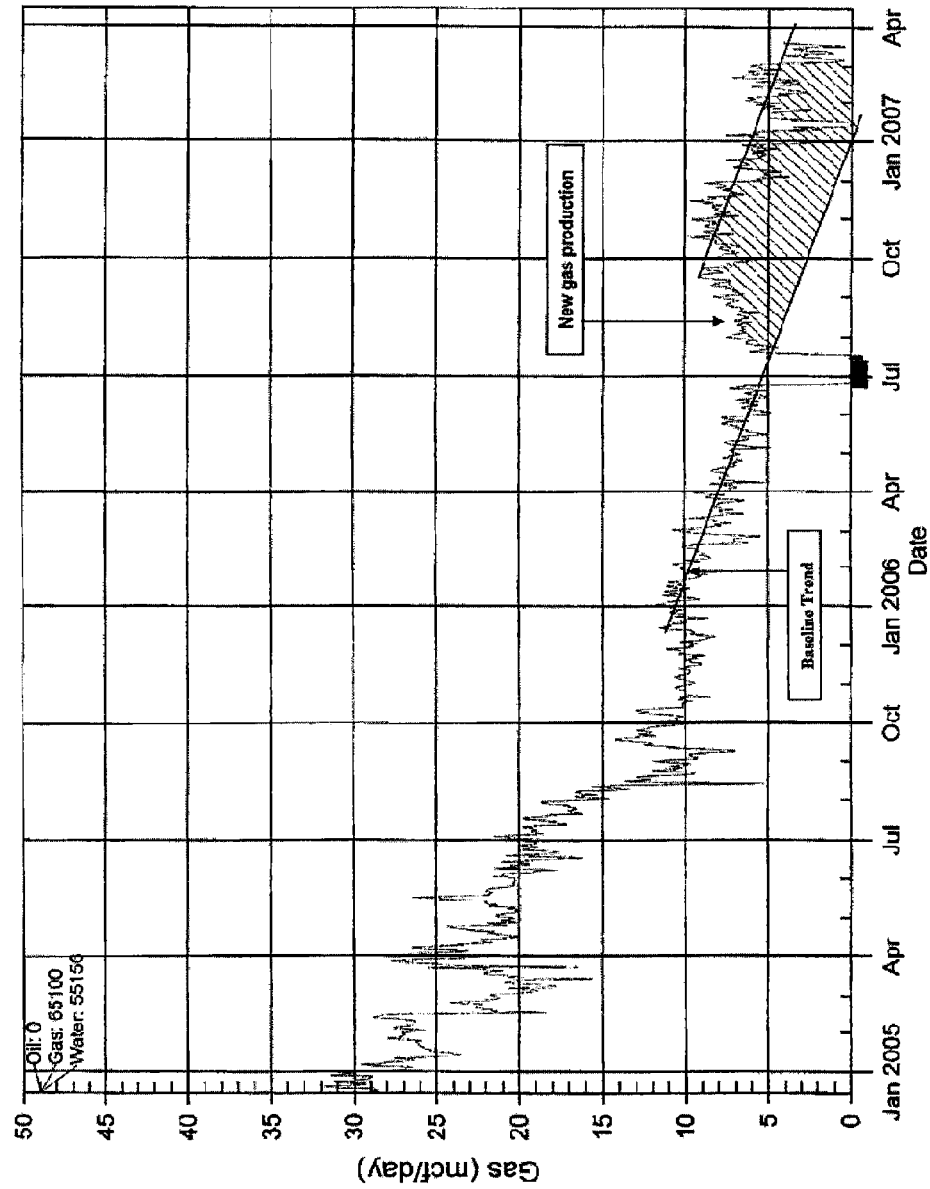
FIG. 16 is a graph of measurements of natural gas production over time from a coal formation before and after an amendment of acetate was introduced to the formation.

Referring now to FIG. 16, a graph of measurements of natural gas production rates from a coal formation before and after an amendment of acetate is shown. As shown in the left part of FIG. 16, a baseline trend measurement of gas production from the well that was taken over a period of about 1.6 years showed a declining production rate from about 30 mcf/day to about 6 mcf/day.

The gas well was then treated with an amendment of sodium acetate (acetate) mixed with live water that contained microorganisms for about 1 month. The amendment included the introduction of an aqueous solution of 0.0036 M acetic acid (derived from sodium acetate and sodium acetate trihydrate) and live water to the underground formation at a rate of about 19,200 L/day for each day of the treatment period. Following the treatment period with the acetate amendment, the gas well was sealed for a few more days (the dwell period) before the gas rate measurements resumed. Again the measurements show an increase in the rate of natural gas production following the acetate treatment. Similar results were obtained for amendments of phosphate and live water.

Figure 17A:
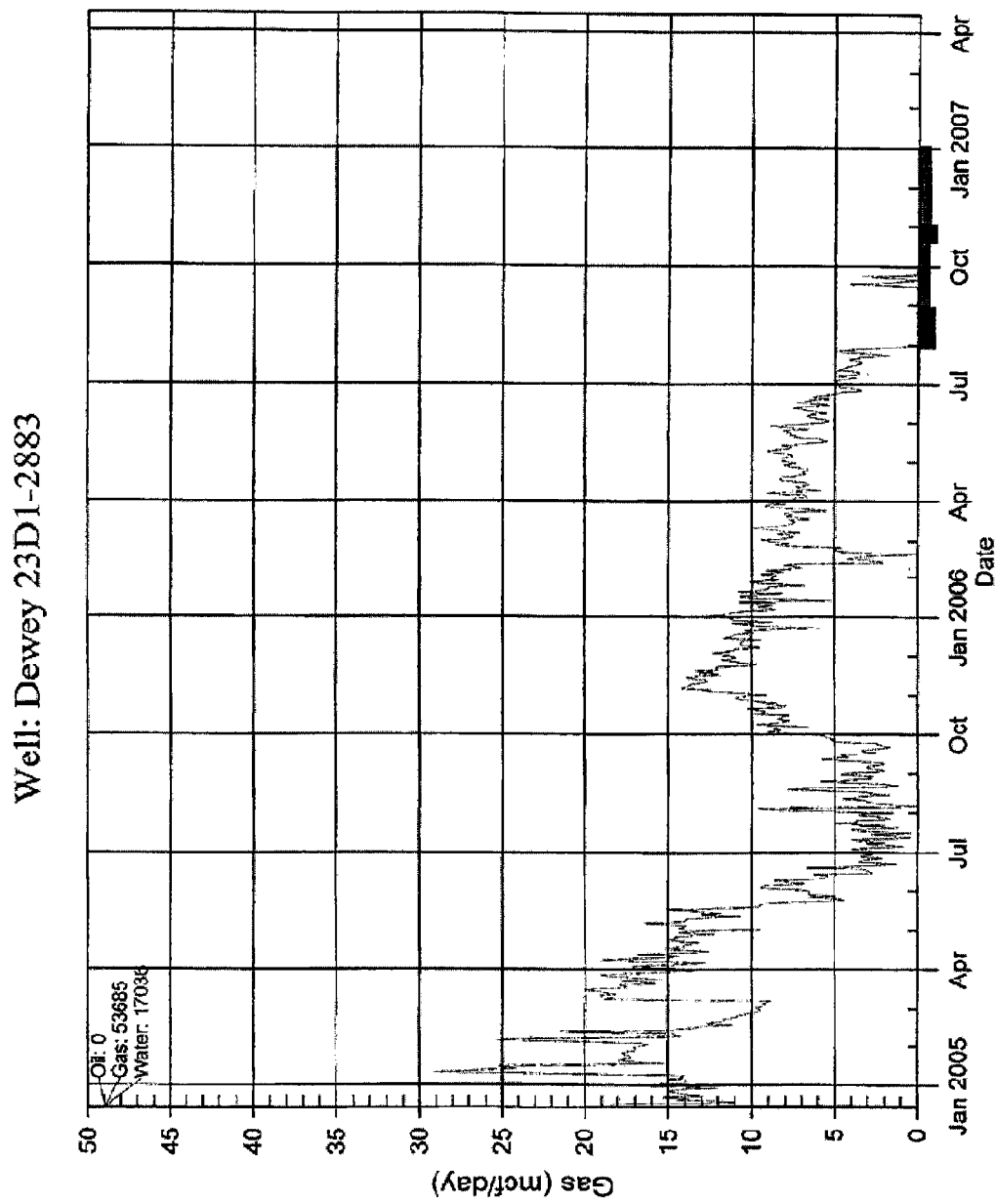
FIGS. 17A-C are graphs of measurements of natural gas production over time from a coal formation before and after the introduction of water filtered to remove microorganisms was introduced to the formation.
Figure 17B:
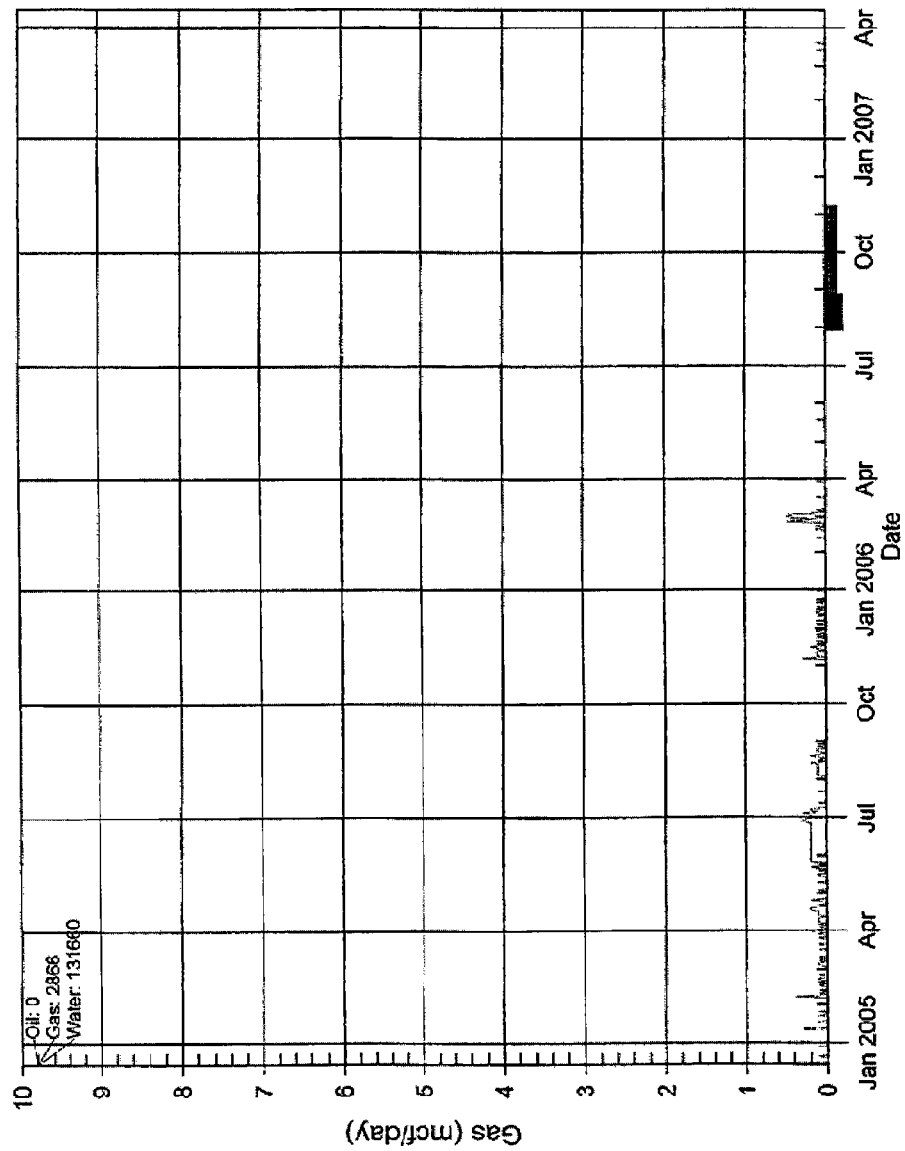
Figure 17C:
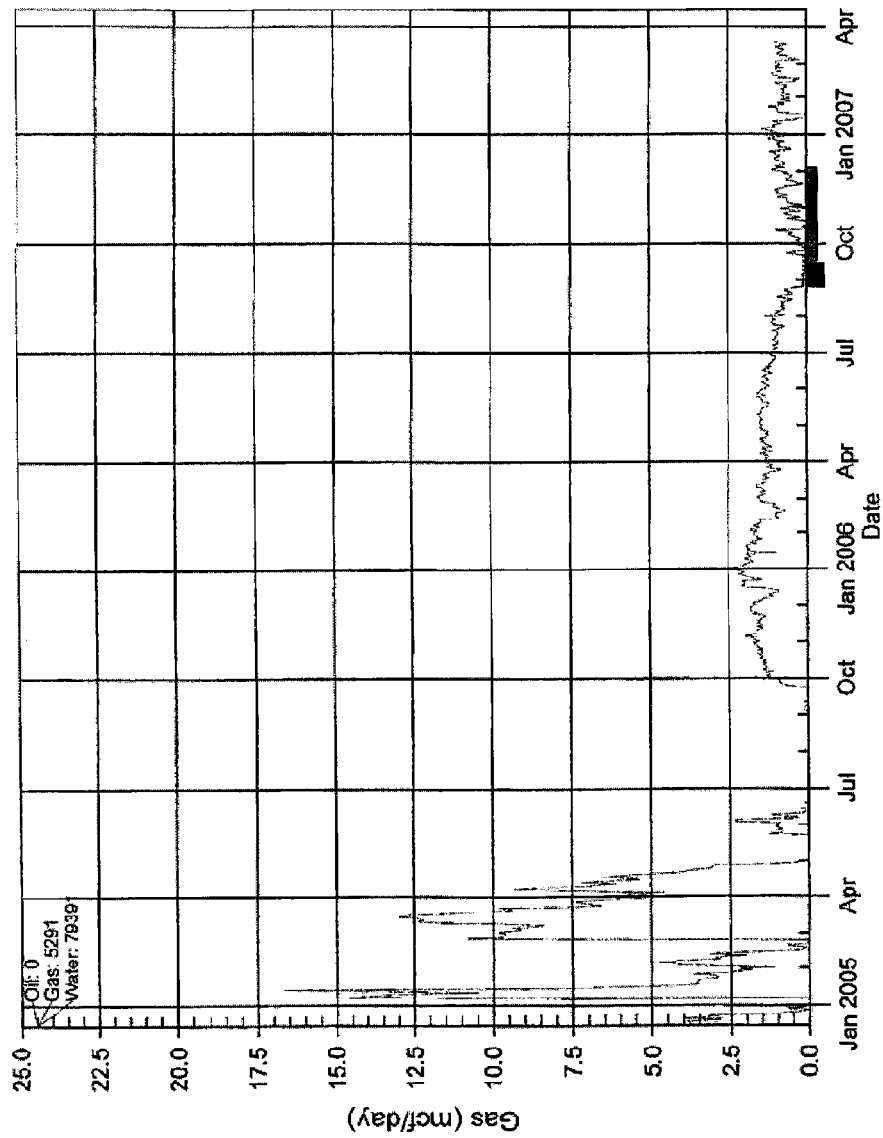

Comparative field tests were also run to confirm that the increase in gas production was not simply due to physical or non-biological chemical processes caused by introduction of additional water to the formation. FIGS. 17A-C are graphs of measurements of methane gas production over time from a coal formation before and after the introduction of filtered water to the formation. In these experiments, formation water was filtered to remove most of the microorganisms before being added to the formation.

FIG. 17A shows a graph plotting the methane production levels before and after treatment with filtered water. A baseline trend measurement of the gas production before the treatment was taken over the course of about 1.75 years and showed a declining production rate from about 15 mcf/day of gas to about 5 mcf/day over the course of the measurement period. The gas well was then treated with an amendment of filtered water for about 1 month (i.e., August) followed by a dwell period of about 1.5 months (September to mid-October). The amendment included the introduction of filtered water at a rate of 36,900 L/day over the course of the treatment period. During and after the dwell period, very little natural gas was detected at all, with most days showing a production rate below the detectable limit.

In response, a second filtered water treatment was performed to introduce additional filtered water to the formation for a period of about 2 weeks (late October), followed by an additional 2 month dwell period (November to January). During and after the dwell period, natural gas was not detected at a production rate above the detectable limit. Thus, an amendment of just filtered water in this field test shows no, or possibly even a negative effect on the rate of natural gas production from the formation.

FIG. 17B graphed the results of a field test where the formation was classified as inactive before the amendment was introduced. As the baseline trend measurement of the gas production rate over the course of about 1.75 years showed, the level of production activity was almost zero, with an occasional short-lived spike above 1-2 mcf/day. The filtered water amendment was introduced to see if water alone could increase gas production from the inactive formation. The amendment introduced filtered water at a rate of 76,600 L/day over a period of about 1 month (August) followed by a 2.5 month dwell period (late August to early November). During and after the dwell period, the amount of natural gas detected remained low, with most days showing a production rate below the detectable limit. Thus, an amendment of just filtered water in this field test shows no ability to increase natural gas production from an inactive formation.

FIG. 17C graphed the results of another field test of a filtered water amendment to a formation with declining natural gas production. As the baseline trend measurement of the gas production rate over the course of about 1.75 years showed, the level of production decreased from peaks of over 15 mcf/day to a level of about 1 mcf/day. The filtered water amendment was introduced to see if water alone could increase gas production from the inactive formation. The amendment introduced filtered water at a rate of 22,100 L/day over a period of about 2 weeks (September) followed by about a 3 month dwell period (September to early December). During and after the dwell period, the amount of natural gas detected dipped and retuned to a level slightly below the pretreatment period (about 1 mcf/day). Thus, an amendment of just filtered water in this field test appears to have had no ability to increase the rate of natural gas production in the formation.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the microorganism" includes reference to one or more microorganisms and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of stimulating biogenic production of a metabolic product with enhanced hydrogen content, the method comprising:
   accessing a consortium of microorganisms in a first geologic formation that includes a carbonaceous material; and
   detecting a plateau in a concentration of the metabolic product with enhanced hydrogen from the first geologic formation that is indicative of a rollover effect;
   providing a nutrient amendment comprising a yeast extract amendment and a phosphate compound in water to the microorganisms in the first geologic formation having the rollover effect,
   wherein the amendment increases the concentration of the metabolic product with enhanced hydrogen content to a level greater than a rollover point where the rollover effect began to occur.

2. The method of claim 1, wherein the yeast extract amendment is brewer's yeast extract.

3. The method of claim 1, wherein the method further comprises extracting a portion of the microorganism consortium from the first geologic formation and introducing it to a second geologic formation.

4. The method of claim 3, wherein the method further comprises extracting a portion of a second microorganism consortium from the second geologic formation and introducing it to a third geologic formation, wherein the second consortium stimulates the biogenic production of the metabolic product in the third geologic formation.

5. The method of claim 4, wherein the method further comprises extracting microorganisms from the second or the third geological formation and introducing them into the first geologic formation after said extraction of the microorganism consortium from the first geologic formation.

6. The method of claim 1, wherein the phosphorous compound comprises an alkali metal phosphate.

7. The method of claim 1, wherein the nutrient amendment further comprises a carboxylate compound.

8. The method of claim 7, wherein the carboxylate compound comprises an acetate compound.

9. The method of claim 1, wherein the metabolic product with enhanced hydrogen content comprises a component of natural gas.

10. The method of claim 1, wherein the metabolic product with enhanced hydrogen content comprises methane.

\* \* \* \* \*